(12) United States Patent
Livingston

(10) Patent No.: US 6,999,553 B2
(45) Date of Patent: Feb. 14, 2006

(54) METHOD AND APPARATUS FOR X-RAY MAMMOGRAPHY IMAGING

(75) Inventor: Troy Livingston, Northbrook, IL (US)

(73) Assignee: Livingston Products, Inc., Wheeling, IL (US)

( * ) Notice: Subject to any disclaimer, the term of this patent is extended or adjusted under 35 U.S.C. 154(b) by 0 days.

(21) Appl. No.: 10/705,760

(22) Filed: Nov. 10, 2003

(65) Prior Publication Data

US 2005/0008117 A1  Jan. 13, 2005

Related U.S. Application Data

(60) Provisional application No. 60/511,593, filed on Oct. 15, 2003, provisional application No. 60/451,777, filed on Mar. 4, 2003.

(51) Int. Cl.
*A61B 6/04* (2006.01)

(52) U.S. Cl. .......................................... 378/37; 378/177

(58) Field of Classification Search .................. 378/37, 378/208, 177, 179, 195
See application file for complete search history.

(56) References Cited

U.S. PATENT DOCUMENTS

| | | | | |
|---|---|---|---|---|
| 4,943,986 A | * | 7/1990 | Barbarisi | 378/37 |
| 5,050,197 A | * | 9/1991 | Virta et al. | 378/37 |
| 5,506,877 A | * | 4/1996 | Niklason et al. | 378/37 |

* cited by examiner

*Primary Examiner*—David V. Bruce
*Assistant Examiner*—Hoon Song
(74) *Attorney, Agent, or Firm*—Fitch, Even, Tabin & Flannery

(57) ABSTRACT

A mammographic method and apparatus are provided for obtaining improved compression of posterior, middle and anterior breast tissue without pushing posterior breast tissue from the imaging volume and with less discomfiture to the patient. An initial compression of the posterior tissue is achieved by vertical, relative displacement of the paddle relative to the bucky assembly to compress the posterior breast tissue therebetween. Less patient discomfiture is achieved by using an inclined compression surface on the paddle or bucky assembly to compress the anterior and middle breast sufficiently for good X-ray imaging without further displacement of the skin adjacent the chest wall. A horizontal force component inclined force will not push the posterior compressed breast tissue from the imaging area. Herein a paddle may have a posterior breast section and have a flexed section which is biased to engage and conform to the breast shape. The flexed section may be releasably held by a lock and then released to apply compression forces to the middle and anterior breast. The flexed section is guided to remain level and to uniformly compress breasts which are not centered thereunder and without binding. The buckey assembly may have a hinged inclined section to compress the middle and anterior portions of the breast. The entire bucky assembly may be hinged to raise the image detector thereon and thereby lessen the heel effect. Alternatively, the bucky cover may be hinged to swing upwardly into an inclined position to compress the middle and anterior breast portions while the image detector is not.

55 Claims, 20 Drawing Sheets

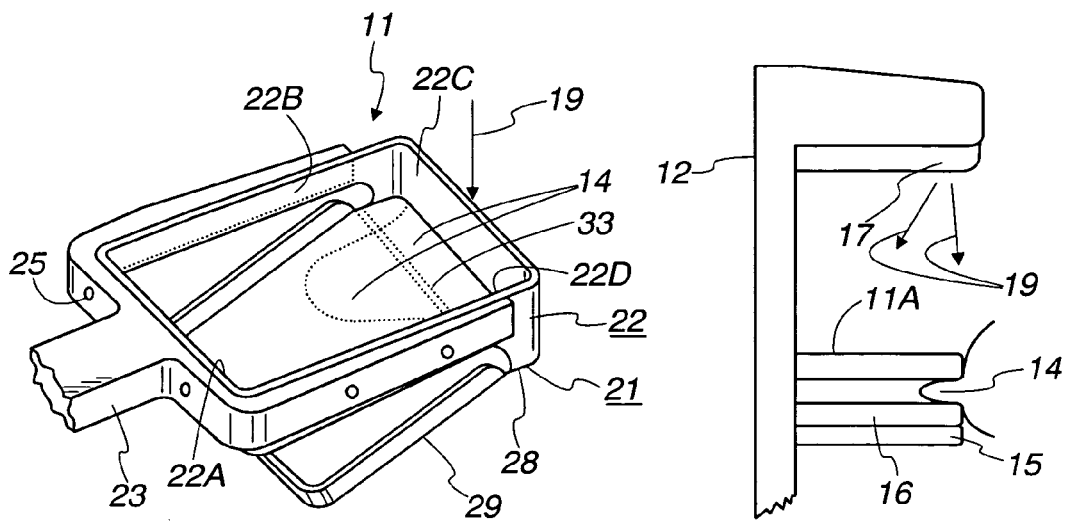
Fig. 1
Fig. 2
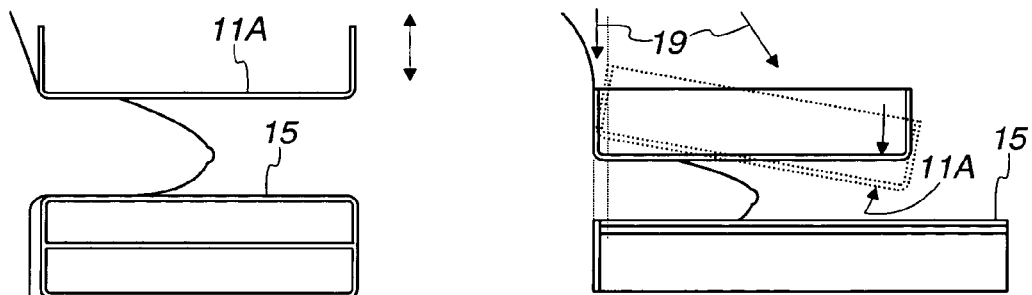
Fig. 3
PRIOR ART
Fig. 5
PRIOR ART
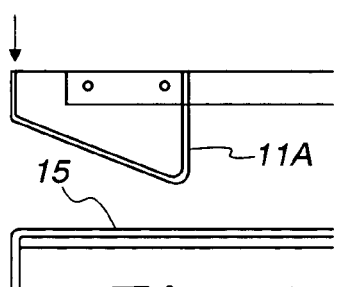
Fig. 4
PRIOR ART
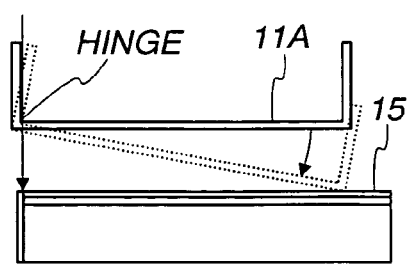
Fig. 6
PRIOR ART

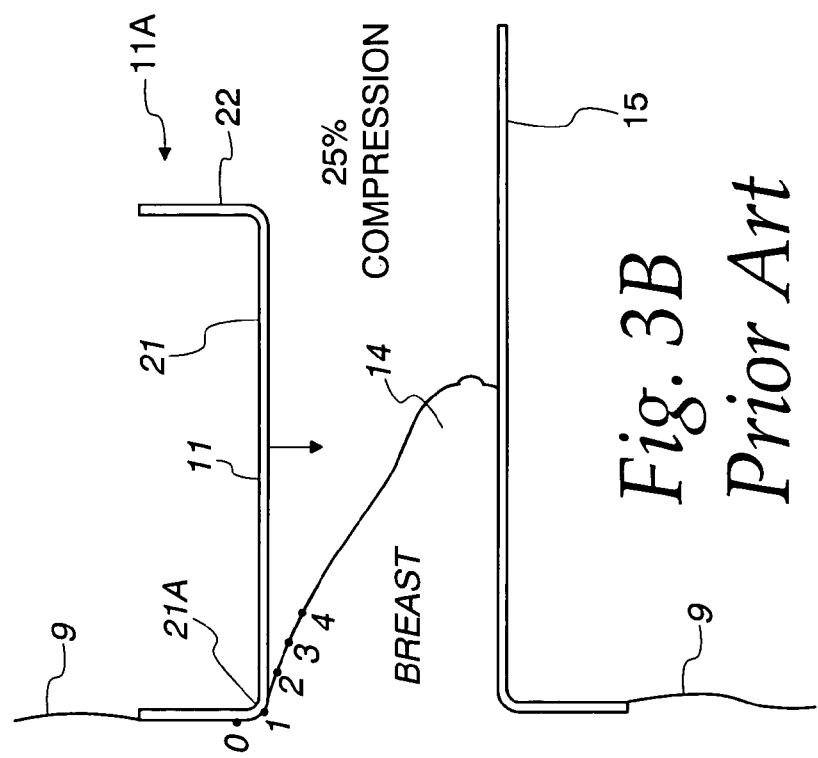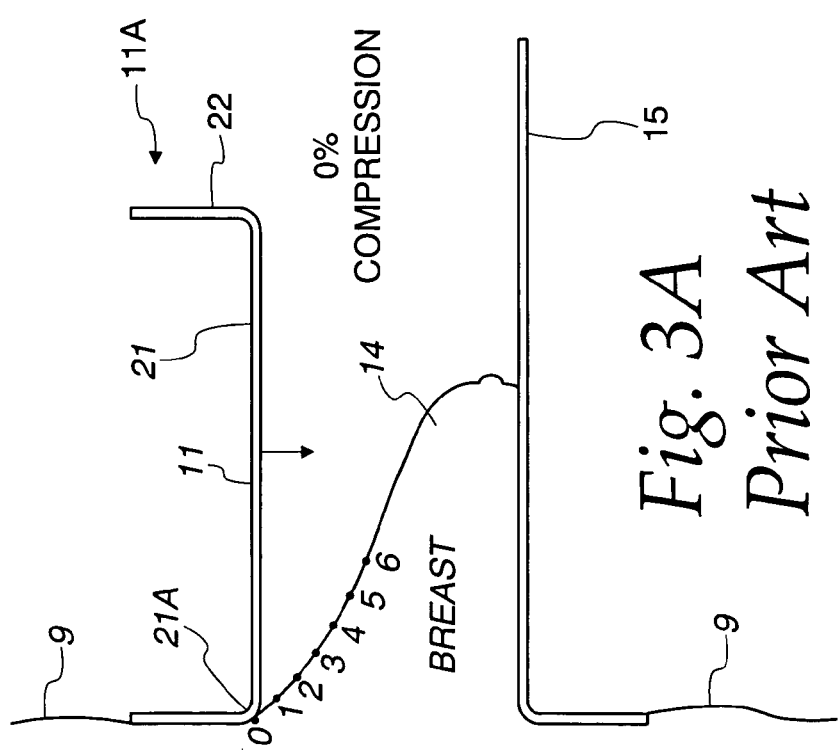

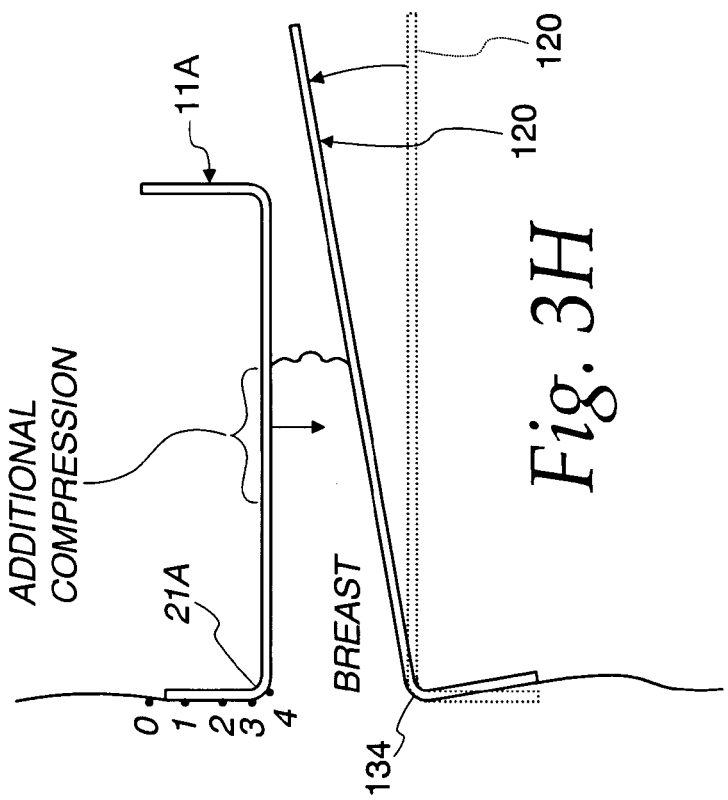
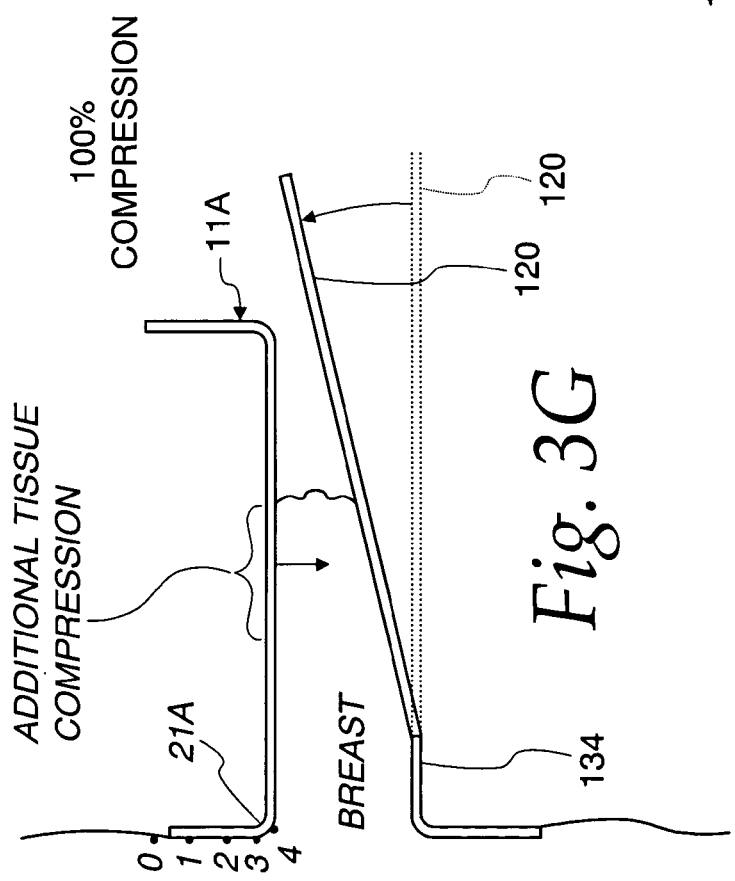

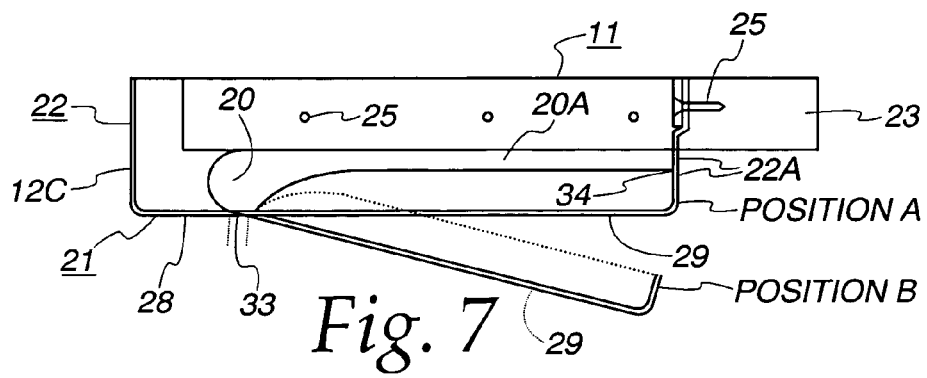
Fig. 7
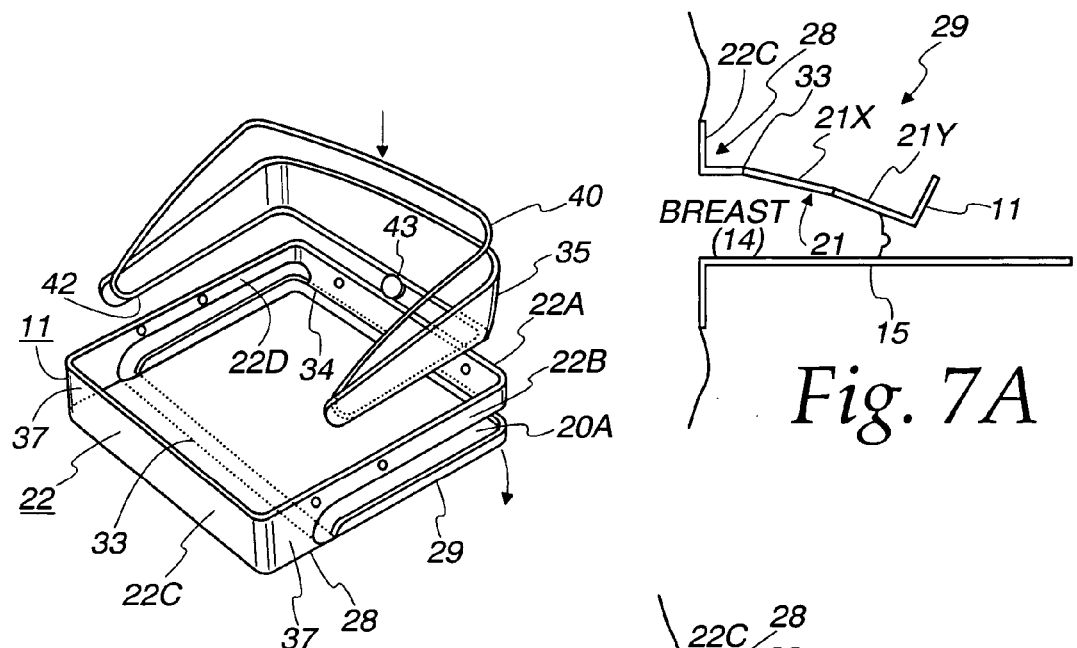
Fig. 7A
Fig. 8
Fig. 7B
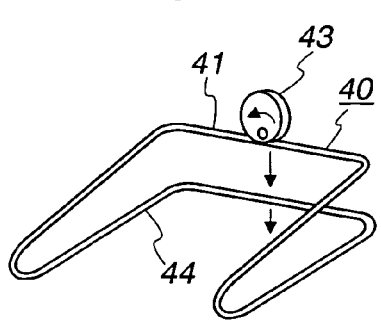
Fig. 9

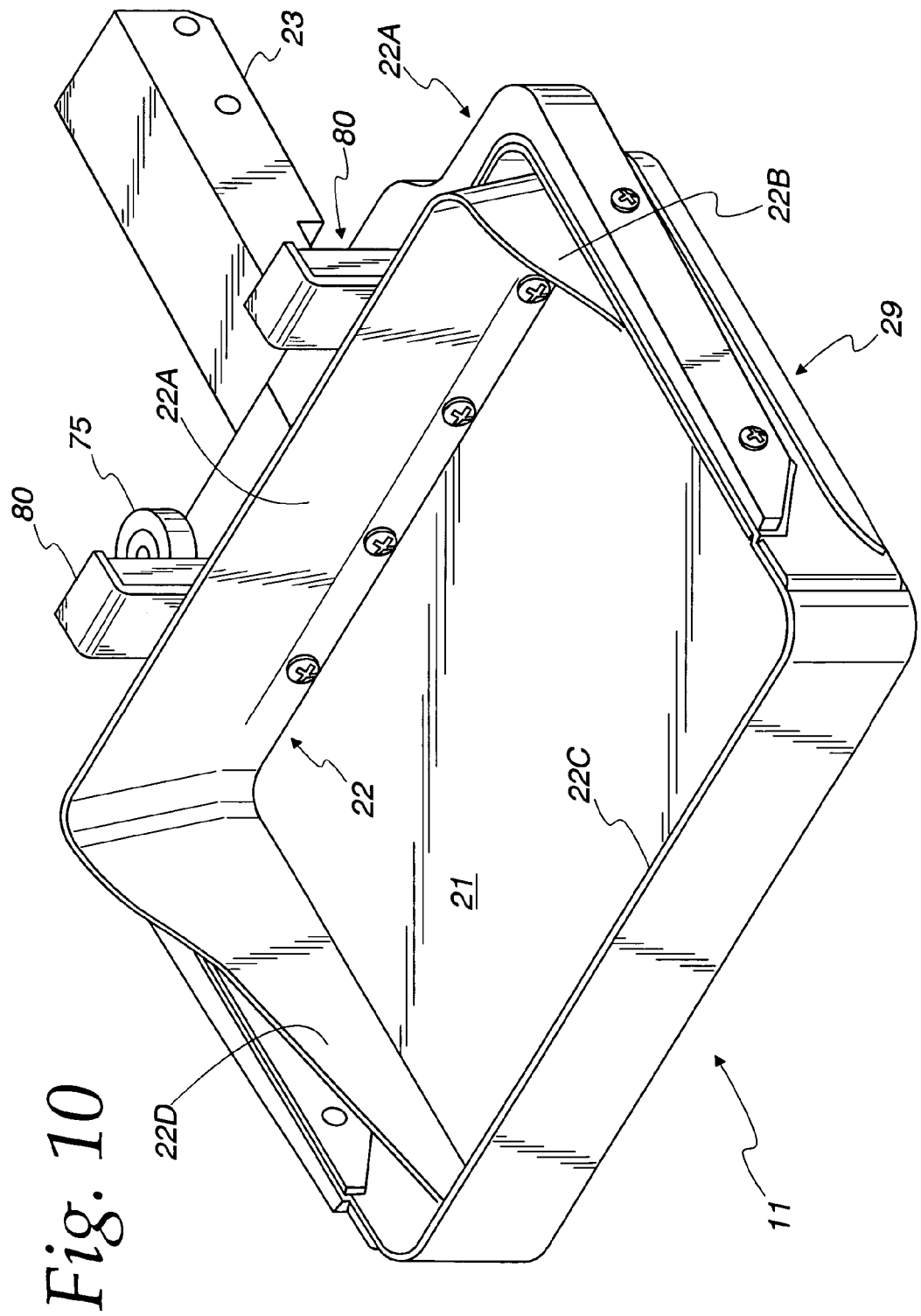

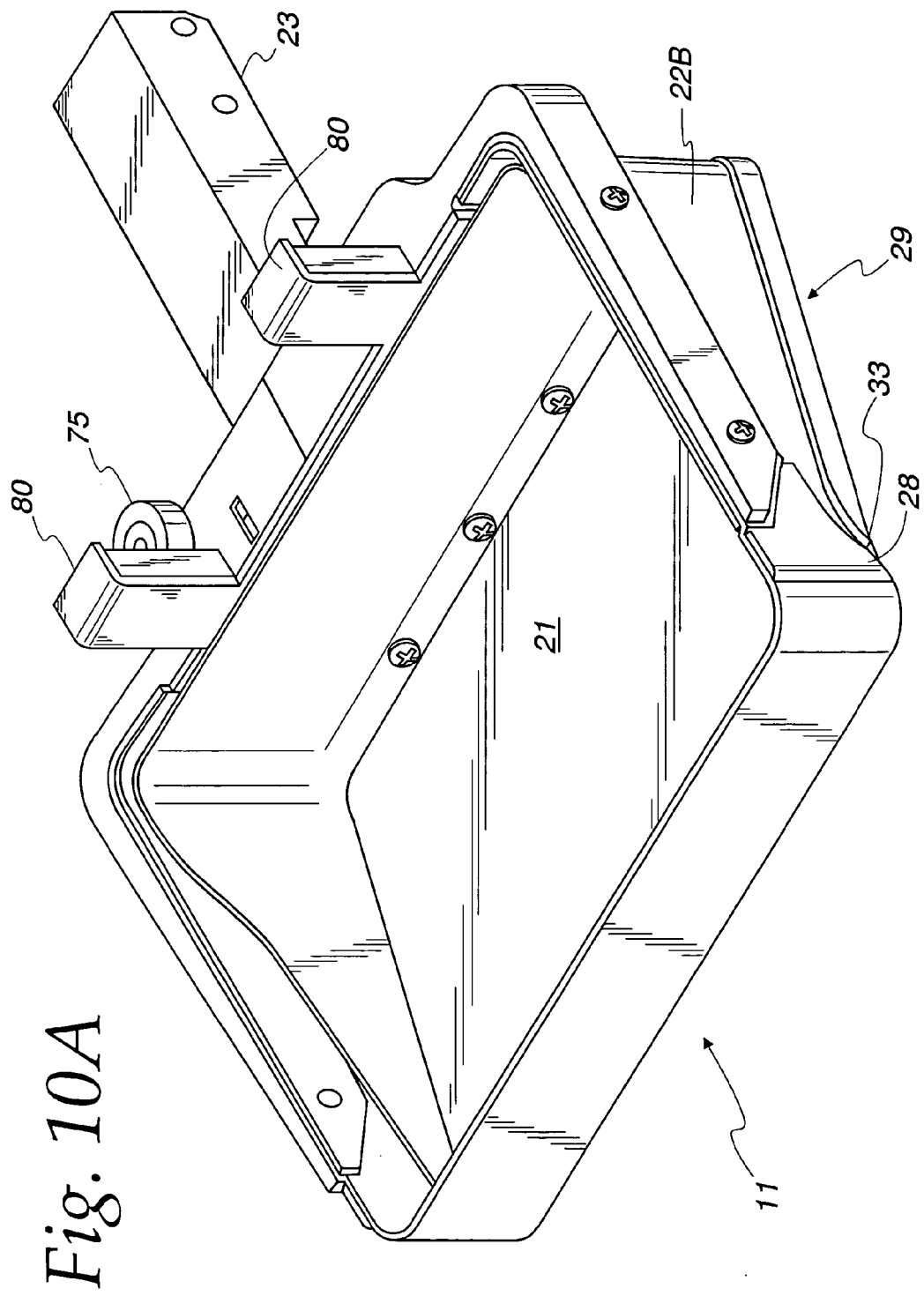

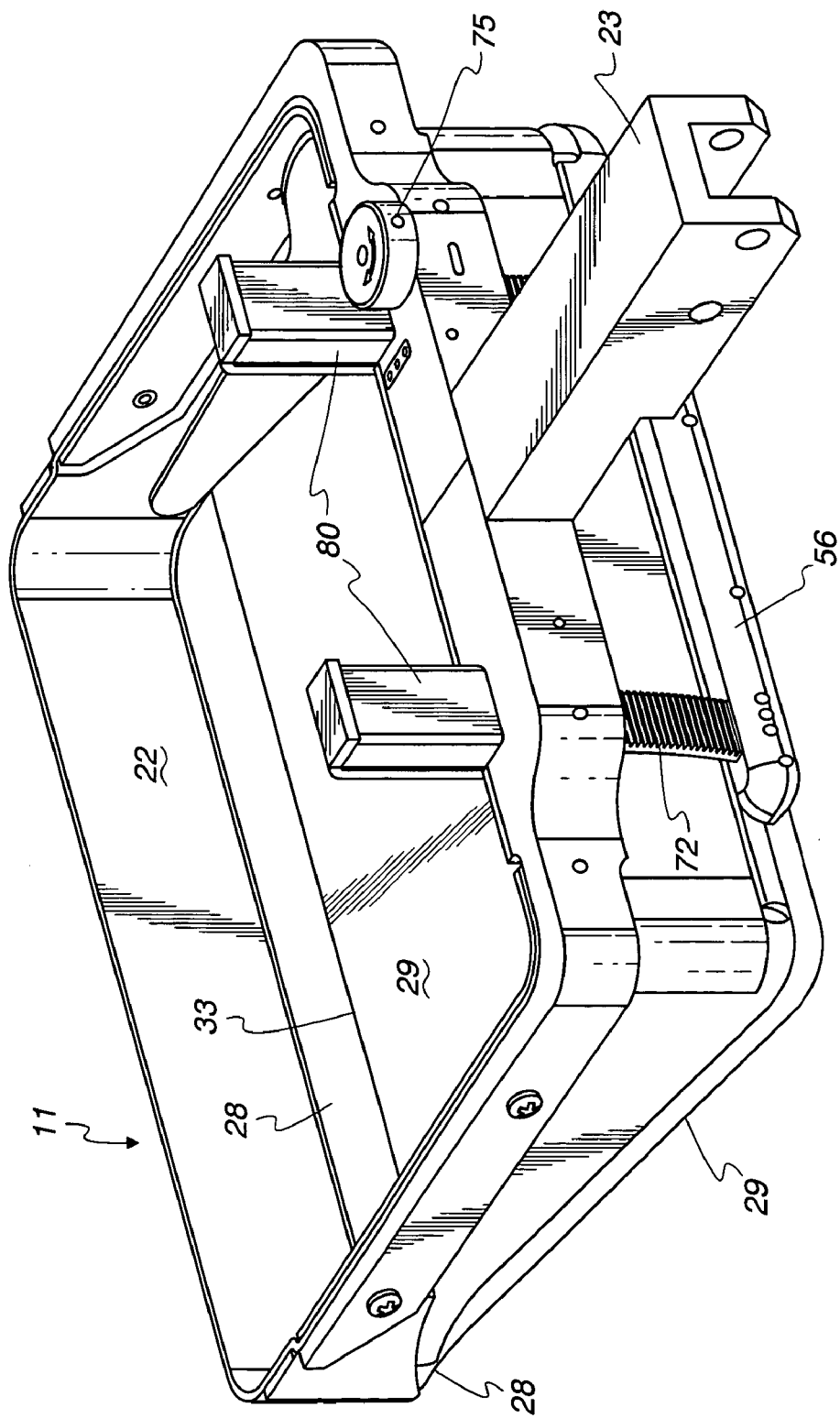

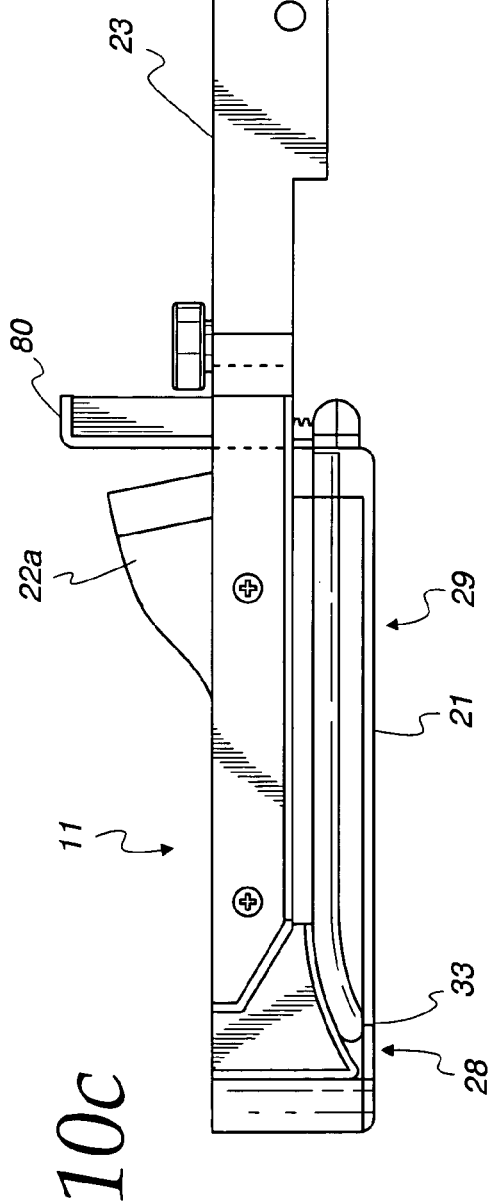
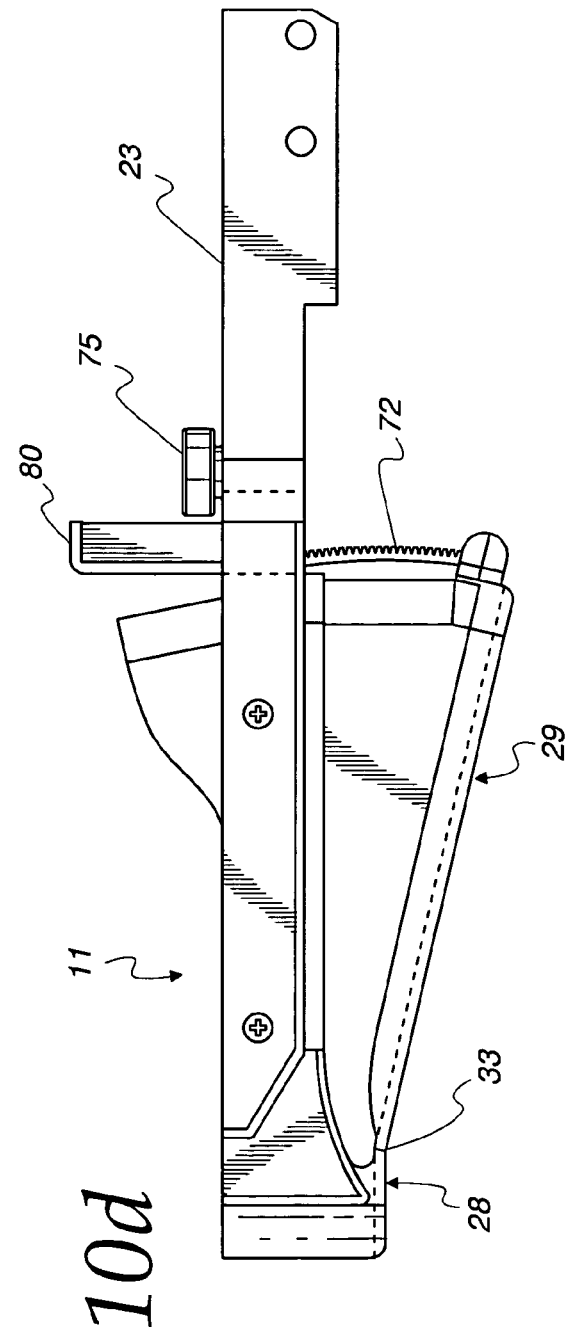
Fig. 10c
Fig. 10d

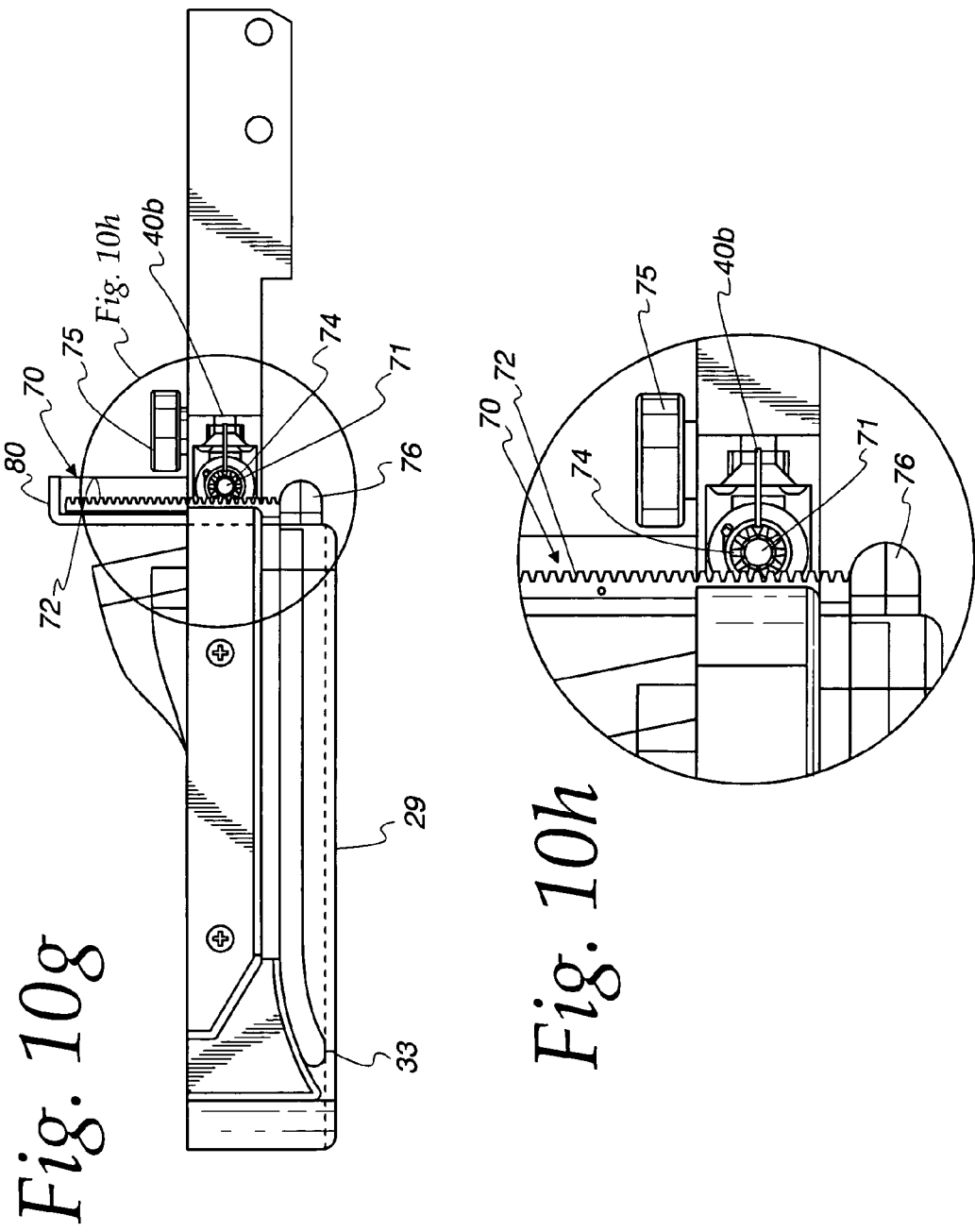

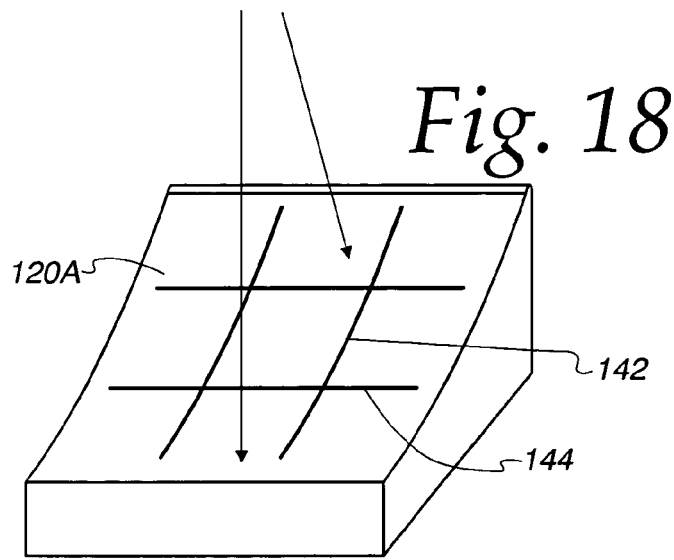
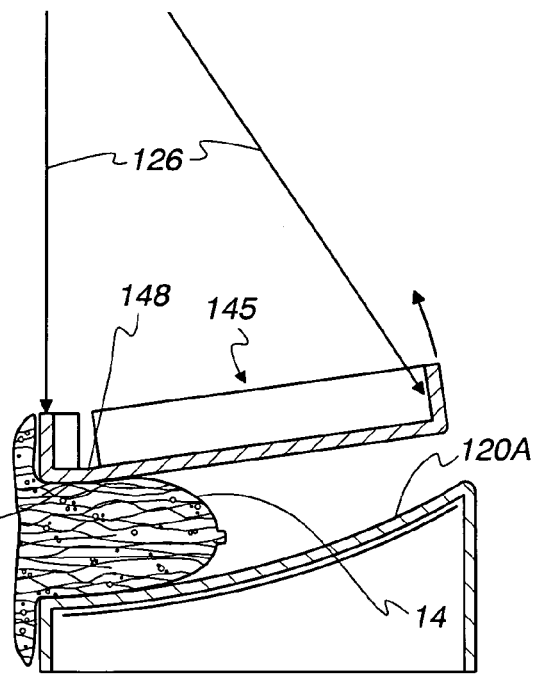
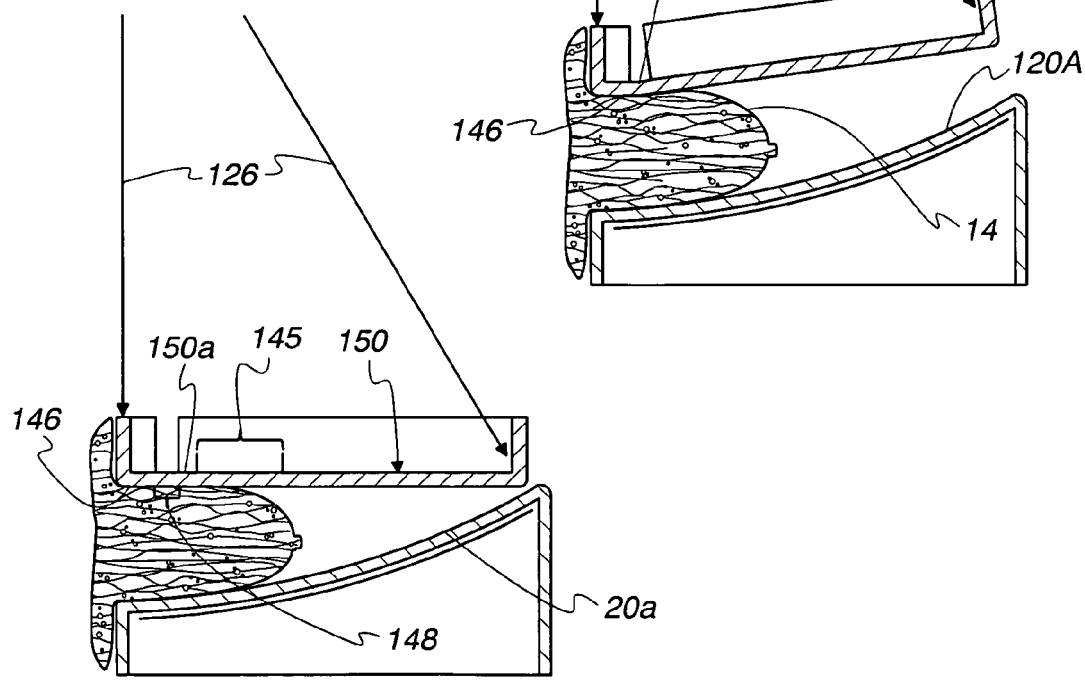

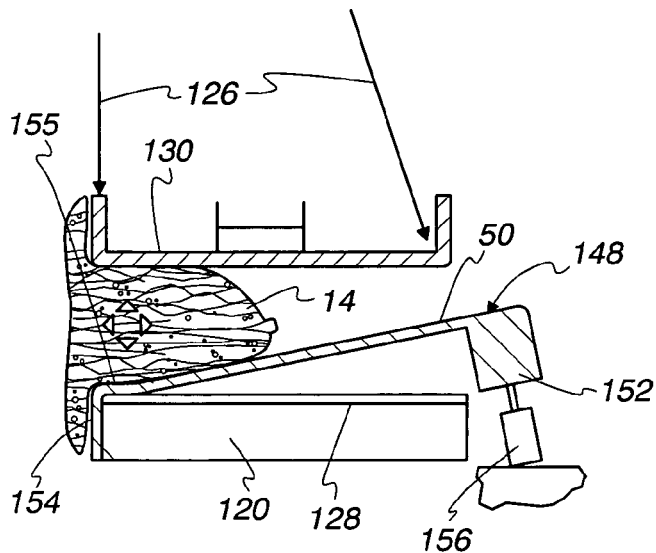
*Fig. 22b*
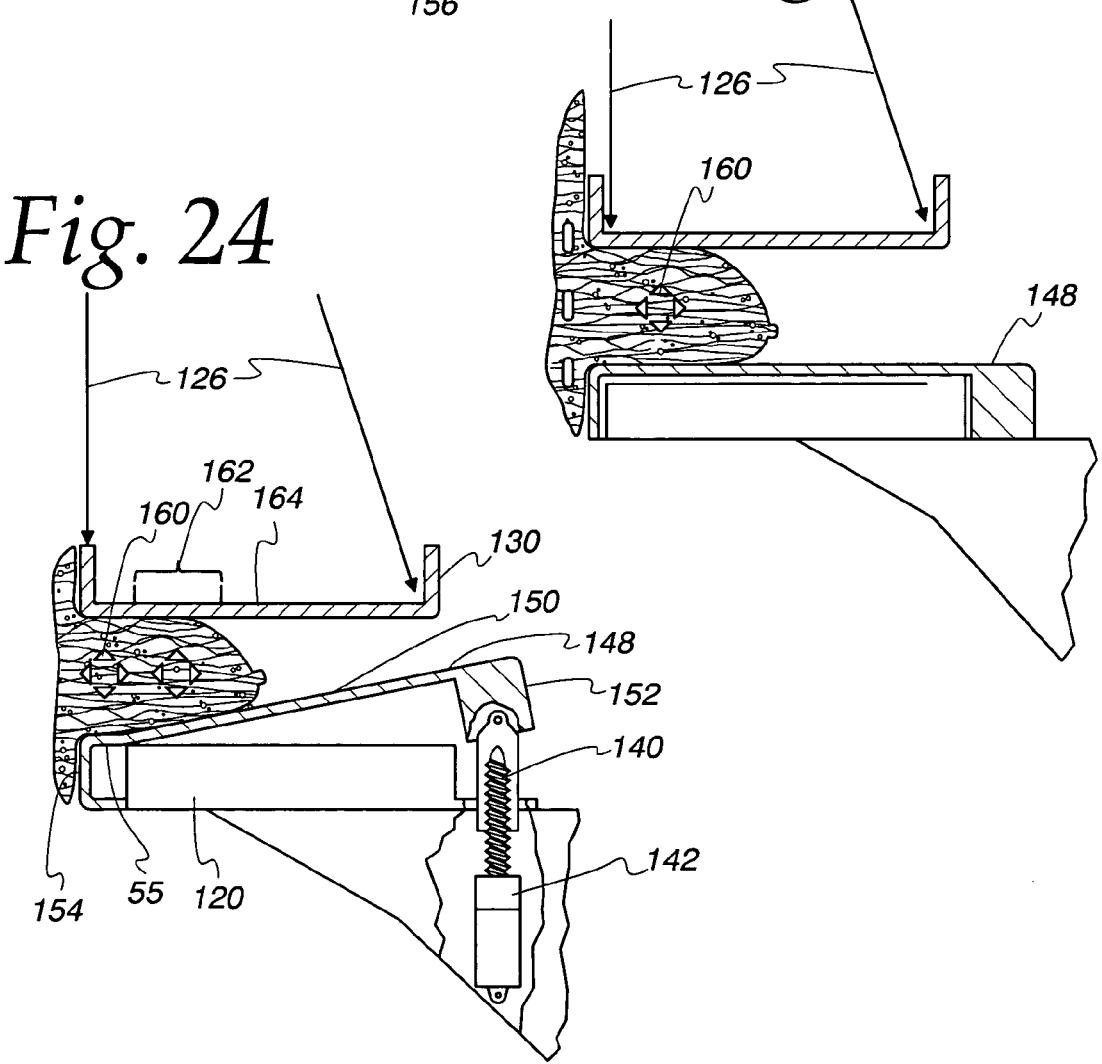
*Fig. 23*
*Fig. 24*

METHOD AND APPARATUS FOR X-RAY MAMMOGRAPHY IMAGING

This application claims the benefit of U.S. Provisional Patent Application No. 60/451,777; Filed: Mar. 4, 2003 and U.S. Provisional Patent Application No. 60/511,593; Filed: Oct. 15, 2003; entitled "Mammography System."

FIELD OF THE INVENTION

This invention relates to a method and apparatus for use in breast mammography and also to a compression paddle and a bucky therefor.

BACKGROUND OF THE INVENTION

In mammography systems the most commonly used compression device includes a compression paddle which is parallel to an image detector on a bucky and the paddle is moved vertically relative to the bucky with a patient's breast therebetween to compress the breast. The compressed breast is then exposed to x-rays to obtain a mammography image on a film or on a digital detector such as a semi-conductor detector. Compression of the breast enables better x-ray imaging because the breast is thinner, the breast tissue is spread, there are fewer superimposed layers of tissue in the image. The breast is usually most thick at the chest wall and thinner at the anterior nipple end and a substantial difference in compression results between the posterior and anterior breast portions with less force and compression at the thinner anterior portion. The imaging quality of the less compressed breast suffers.

It has been recognized and proposed in several devices to supplant the known system for other non-parallel paddle systems such as disclosed in U.S. Pat. No. 5,506,877; U.S. Pat. No. 5,706,327 and in a paddle being sold by American Mammographics of Chattanooga, Tenn. These prior art proposals have a number of serious shortcomings which will become apparent from the following discussion relative to compression of the breast in a mammography operation. The posterior breast portion may be more denser and/or more thick at the chest wall than at the nipple end, or there may be a breast implant at the chest wall, or pectoral muscle that interferes with a proper compression of the posterior portion of the breast.

A mammography system is most effective, in detecting lesions in fatty breasts and is the least effective in very dense breasts. In some tests it appears that the sensitivity to detection of the presence of a benign lesion or malignant lesion drops almost in half where the breast is extremely dense. That is, a progressive decrease in mammography sensitivity results as the breast density increases. Furthermore, often the majority of the missed cancers are located in the middle of the breast where the compression with the parallel technique above described using a conventional, horizontal compression paddle because there is relatively less compression at the middle portion and also at the anterior portion than at the chest wall portion of the breast. Often the lesions or calcites are closely adjacent to the chest wall and may be superimposed close to the chest wall. If these superimposed calcites are not spread or, if they are pushed back into the chest wall out of the imaging area, the chance of a cancer being missed will be greatly increased.

To improve the image quality so that cancers will not be missed, there is a need to lesson imaging deficiencies such as an unsharpness of the lesion, poor contrast of the lesion, and a failure to spread apart the fiberal glandular tissues to show superimposed portions of the lesions. Inadequate compression appears to be the underlying cause of many of these imaging deficiencies and a better improved compression should prevent the unsharpness by reducing breast thickness to allow shorter exposure times and a loss of sharpness due to the motion of the patient while in the mammography machine.

With respect to resolution or contrast, there is a minimal standard of being able to see eleven pairs of lines per millimeter. It has been reported that Residents or others being trained in the art of viewing mammography images find them difficult because of the relatively poor image quality and because the responsibility for failure to detect the cancer has serious result and a misdiagnosis of a benign area causes the patient to be brought back for further mammography or biopsies. Hence, the image details that need to be interpreted are very essential to the initial decision as to whether the breast is normal or abnormal and if it is abnormal, to require further action between the patient and doctor.

The prior art American Mammography paddle is a rigid paddle that has no rotating or swinging parts but has a gently curved compression surface that slopes downward towards the nipple. As the paddle is lowered the curved compression surface is said to contact the breast between the chest wall and the anterior portion. The rigid inclined posterior portion of the paddle as illustrated in FIG. 4 of this application has a horizontal force component that pushes posterior breast tissue into the chest wall and from the imaging area. Another problem with the non-rotatable American Mammography paddle is that it is difficult for the operator to use in that the operator cannot readily insert the operator's fingers between this lowered compression surface and the underlying bucky in order to grip the breast and pull it away from the chest wall because of the large downward force at the anterior end of this rigid paddle surface. The paddle actually grips the operator's fingers as the breast is pulled and reduced in thickness allowing the anterior end of this rigid paddle to pinch the inserted fingers. This makes it too difficult to shift or spread the tissue manually during the breast compression. More specifically, an operator will pull the breast away from the chest wall with the operator's fingers as the breast is being compressed to prevent tissue from being pushed back into the chest wall and from the imaging area. The inserted fingers are caught by the further downward shifting of the paddle's nipple end as the pulled breast reduces in thickness under this manual pulling.

Because the operators are under typical production quotas in the mammography offices where the mammographies are performed, the operators may not insert their fingers to pull tissue forwardly where the American Mammography paddle is used. The mammography production desired by many most offices is to take four views per patient within a period of about 15 minutes, so that approximately four patients per hour are run through the mammography machines.

Now there has been a general recognition that good and more uniform compression is most desirable in mammography systems, as also a recognition that the proposed systems should address the issue of less patient's discomfort because many of the patient's find the mammography operation to be painful. The operator usually pushes the patient toward the machine such that the chest is brought tight against the downwardly moving paddle and close to the ribs. It is because most of the cancers that occur are often located adjacent the chest wall. Such cancers are closer to the lymph nodes.

The proposal of a paddle disclosed in U.S. Pat. No. 5,506,877 is that of a paddle that has not been commercially marketed and has not been viewed in the market place even though the patent application was filed in November of 1994 and granted in April of 1996. It has several embodiments. It is stated that the paddles of these embodiments compress the breast and push the tissue away from the chest wall and into the imaged volume. This may occur initially but when the angled portion 48c (FIG. 8A) and the curved portion (FIG. 4) adjacent the chest wall are pivoted downwardly to compress the anterior and middle breast tissue they will push the posterior breast tissue into the chest wall and from the imaged volume. The embodiment illustrated in FIG. 3 of the patent has a tray with an upwardly, vertically extending chest wall part 48b on the tray and a hinged breast portion 48a which overlies the top of the breast and which is hinged at 52 and is pulled downwardly by a motorized mechanism. In this FIG. 3 embodiment, the hinge 52 which is located right at a critical area of the chest wall where most of the lesions are found. The vertical chest wall part 48b has a lower, thin edge that engages and compresses the breast along a thin straight line, which although not a knife edge, applies the vertical compressing over a very narrow thin line area. High breast compression at such a thin area of the breast may cause some considerable pain because the tissue is unable to stretch, as will now be explained.

With the conventional horizontal paddle, the breast is often over-compressed at the posterior portion of the breast in order to compress the middle and anterior regions of the breast. In order to get the anterior portion sufficient compression in these women, the operator keeps moving the paddle downwardly until there is such pain that the patient demands that the compression cease. It is not uncommon in this instance, that a red line or even a blood blister is seen at the top of the breast after the breast is removed from the machine. The red line is the result of hemorrhaging or breaking of capillaries.

It has been discovered that such pain is not the result of the compression of this posterior breast tissue beneath the skin, but it is the result of tearing of the skin which does not stretch substantially. As the chest wall end of the paddle slides down the chest wall, the skin located several centimeters from the chest wall must slide back under the descending posterior end of the paddle. The problem is that in order to get sufficient compression at the middle and anterior portions of the breast, the operator having already compressed the posterior sufficiently for good imaging, further lowers this paddle corner until sufficient compression of the anterior region is achieved. It is this last downward movement that the pain is most severe and which is a result of the tearing of the skin as the hemorrhaging occurs. By way of specific example only, if the posterior paddle descends 6 centimeters and achieves sufficient posterior compression for good imaging and the operator lowers the posterior paddle corner another three centimeters to obtain sufficient middle and anterior compression, this additional displacement causes the pain due to tearing of the displaced, non-stretchable skin. The apparatus and method of the present invention overcomes the above-described problem by achieving sufficient compression of the middle and anterior breast tissue to hold the tissue against pushing back into the chest or displacement of skin and tissue from the chest wall without the displacement of the skin that causes the pain and/or skin tearing. This is achieved by lowering the preferred paddle to compress the anterior breast portion sufficiently to hold the chest wall tissue against displacement inwardly and to achieve good imaging, e.g., 6 centimeters in this example, and then swinging only the anterior portion of the paddle down to compress the anterior breast portion while the posterior end of the paddle remains stationary and does not descend the additional three centimeters that caused the pain and red line formation. In a paddle embodiment illustrated and described herein, the posterior paddle end extends horizontally for about two centimeters and this provides sufficient area across the posterior breast to apply the desired initial posterior breast compression without pushing the posterior breast tissue towards the chest wall and from the imaging area as illustrated in FIG. 4. After this chest wall compression by lowering the paddle, e.g., at 6 centimeters, then the operator swings a middle and anterior breast portions downwardly to compress the anterior and middle breast portions sufficiently for good imaging. The amount of force applied at the anterior end is from a spring force biasing the anterior paddle portion downwardly in one embodiment and by an operator controlled motor drive in another embodiment. In the former case, if the operator desires to further compress the middle or anterior breast portions, the operator may apply additional pressure by manually swinging the inclined portion further in the downward direction and then locking the anterior portion in this position while imaging the breast. This additional anterior compression is done without shifting further downwardly the posterior paddle end with a concomitant and further displacing the skin at the chest wall thereby resulting in additional pain or discomfort to the patient.

Returning to the paddle 48 disclosed in U.S. Pat. No. 5,506,877, this paddle 48 is rotatable in several directions by having the first pivot 52 and a second pivot 58. The latter is a centrally located pivot axis and is used to pivot the entire paddle for axilla-inferior imaging of the breast.

Also, Adamkowski et al., U.S. Pat. No. 5,706,327, discloses pivoting about a centrally located pivot axis and in this patent the compression force at the chest wall has a horizontal component pushing posterior tissue toward the ribs and from the imaging volume or area. This patent claims that the paddle is substantially horizontal with respect to the detector at imaging and hence does not recognize that the heel effect problem of imaging of the anterior breast can be alleviated by pivoting the anterior end of the bucky, and the detector thereon, into an angled, non-parallel relationship with respect to the paddle, which will be described in greater detail hereinafter in relationship to the description of an embodiment of the invention.

The present invention also addresses the problem of how to readily and inexpensively retrofit existing mammography machines to improve the quality of imaging and provide less discomfort to the patient. The paddle system illustrated in U.S. Pat. No. 5,506,877 employs a complicated, expensive motor drive and sensor system to drive the hinged portion downwardly to compress the anterior breast portion. Many, if not most owners of existing machines will be reluctant to pay for and to install such an extensive motor drive and sensor retrofitting of their machines. It is stated in this patent that the operator may manually pull the hinged portion downwardly to compress the middle and anterior breast portions. Neither way of operation provides a paddle assembly having an internally biased hinged section that is merely released to compress the breast with desired compression force as is done in one embodiment of the invention. Where an automated paddle drive is desired, the paddle can be driven, as discussed hereinafter with another embodiment of this invention.

There is a need for an improved system that provides good compression across the posterior, middle and anterior breast portions to improve imaging and a need to reduce discomfiture of the patient.

SUMMARY OF THE INVENTION

In accordance with a preferred embodiment, there is provided an improved method and apparatus for compressing substantially the posterior breast at a location adjacent the chest wall and to stabilize this tissue while in a compressed state without pushing of the posterior breast tissue back into the chest wall and from the imaging area, and then to compress the middle and anterior tissue with an inclined portion providing a substantial compression of the middle and anterior breast over a wide range of sizes, shapes and densities of breasts without an interfering shadow in the imaging area and without pushing the posterior tissue back into the chest wall and from the imaging area. Preferably, this is achieved by a patient and operator user-friendly method with less discomfiture to the patient. By way of an example only, the initial compression of the posterior breast tissue at the chest wall between the paddle and bucky is achieved by the paddle traveling downwardly through about six centimeters without the patient feeling any significant discomfiture; and then rather than displacing the paddle vertically relative to the bucky where the patient feels significant discomfiture and/or pain, the posterior ends of the bucky and paddle remain at this 6 centimeter displacement and an inclined portion on the paddle or bucky is swung to compress the middle and anterior breast portions.

In the preferred embodiment, an initial relative movement between the paddle and buckey and the chest wall and the posterior breast tissue is compressed and stabilized without pushing posterior breast tissue from the imaging volume and into the chest wall and maintains this compression such that a subsequent horizontal force component of the compressive force being applied to the middle and anterior breast by the inclined portion and does not push the posterior breast tissue from the imaging volume. That is, the anterior and middle breast compressing force, for example, 10 to 20 pounds of force has a horizontal component or vector of force which ties to push the posterior breast tissue towards the chest wall and thereby from the imaging area. Because of the substantial, initial compression of the posterior breast tissue, this horizontal force and vector is not effective to push the compressed posterior breast tissue laterally into the chest wall and from the imaging volume.

In a preferred embodiment, this compression results in a substantial reduction of breast thickness at the chest wall, the middle, and the anterior portions of the breast which keeps the posterior breast immobilized while still allowing a gripping and manipulation of the breast by the fingers of the operator to pull and to properly position the breast. Preferably one should be able to manipulate the breast much in the manner that is done with the conventional parallel compression paddle and bucky. As will be explained in greater detail hereinafter, the preferred paddle embodiment has a spring force of e.g., 10 to 15 pounds that will be applied to the operator's fingers. Hence, the operator can, despite this relatively light pressure on the fingers, grip and manipulate tissue at the bottom of the breast and prevent the nipple from folding under in the final compression because the operator's fingers can move and remain under the anterior portion of the paddle even though the anterior portion is being compressed. There is no need as in the conventional horizontal paddle to raise the paddle and release the posterior compression in order to spread the breast.

There is less discomfiture with the paddle of this invention than in the parallel bucky and paddle of the prior art because the conventional paddle is typically lowered an additional 2 or 3 centimeters at the chest wall, compared to the paddle of this invention, in order to compress the anterior breast. In the preferred paddle the swinging of the inclined portion compresses the middle and anterior breast without requiring the additional downward displacement of the posterior end of the paddle in order to compress the anterior breast portion. Because the skin covering the posterior breast tissue at the chest wall will have already been displaced and be taut, the additional downward travel of the posterior end for another 2 or 3 centimeters results in discomfiture and may result in painful skin tearing, as above described.

Illustrated herein are several different embodiments. The first of which is described hereinafter involves a paddle have a first rigid portion adjacent the chest wall extending horizontally for a predetermined distance to compress the chest wall first or initially thereby to stabilize the posterior tissue at the chest wall without a shifting laterally into and between the ribs and out of the imaging area either during this first initial compression or by a later applied horizontal force component. The inclined portion of the paddle, which is held in an upper horizontal position is released to flex downwardly and thereby further compress the middle and anterior portions of the breast. In this embodiment, the paddle does not compress the chest wall with a thin straight line edge that can result in a red line across the breast or a pushing of posterior tissue or pectoral muscle into the chest wall and from the imaging area.

The preferred paddle has the inclined portion normally held or locked in an upper position with it being generally horizontal with the chest wall portion; and then the flexed, inclined portion is released and pivoted by a biasing force on the paddle which swings the inclined portion down and exerts the compressive force to the middle or the anterior breast portions. In this embodiment, a typical range would be about 25 to 40 pounds of force applied at the chest wall to compress and to stabilize the posterior breast, e.g., over about one inch in width and a biasing force, for example, 10 to 20 pounds is applied by the paddle inclined portion to the smaller anterior breast tissue and about the nipple. If the breast is pear-shaped, very dense or has more tissue at the anterior end than is usual, the operator may manually pull the inclined portion down to exert even greater force to obtain the desired compression. The inclined portion is then locked in this additional force-applying position during the imaging operation.

Herein, the illustrated inclined portion is guided to compress with an even force for those breasts that are off center to the left or right of the paddle center line and to do so while the inclined section is held level and does not bind because of the off-center positioning of the breast between the paddle and the bucky. That is, the preferred paddle does not require breast centering under the paddle. Effective compression surfaces across the width of the paddle remain level at all tilt angles allowing for off-center breast positioning. Moreover, large breasts can be imaged without having to change to a second paddle.

In another embodiment using this paddle, the operator may have a motorized drive operated by a manual control such as a foot pedal, to apply pressure until the person either complains and/or that the operator sees that the anterior and middle portions have been compressed sufficiently. Flexing does not use a typical piano hinge or other occluding thick, hinged portion but uses or is often termed a living hinge of the plastic material itself between the rigid posterior and inclined, pivoted portions of the paddle.

This paddle embodiment has been found to cause little discomfort or pain even though there may be 90 to 120 newtons of force applied at the posterior breast tissue which is first compressed and there may be as much as 110 newtons applied at the hinged portion.

Another embodiment of the invention employs a tilting bucky or support which is located beneath the breast and which can be pivoted upwardly at an angle after it has initially compressed the breast at the chest wall. Herein, in the illustrated embodiment, the posterior tissue is first compressed as the bucky moves vertically upward with its posterior end compressing the tissue at a hinge which can be a large, occluding hinge because it is not between the X-ray source and the detectors. Thus, the bucky hinges are out of the imaging area. A particular advantage of pivoting the anterior end of the bucky to an incline is that it carries the anterior detectors upwardly thereby reducing the heel effect of the longer and more incident X-rays located at the anterior breast. That is, X-rays emanate from a small spot usually located directly over the chest wall portion and the chest wall receives the short, direct X-rays whereas X-rays beams to the anterior nipple end of the breast are at large incident angles. The heel effect is reduced because the anterior breast tissue has been raised with the bucky detector also being raised to shorten its X-ray distance to the detector (S.I.D.). This results in a considerable energy boost at the anterior portion. Stated differently, the X-rays have an energy factor which changes with the square of the distance from the breast tissue to the X-ray spot. In the illustrated embodiment, the pivoting bucky may raise the anterior breast detector, e.g., by 3 to 3.5 centimeters. It is a square of the 3 to 3.5 centimeter that results in a large change in the energy factor because of the raising of the anterior breast detector toward the X-ray energy spot. Because of this heel effect, it has been sometimes hard to get a good X-ray image at the anterior nipple portion of the breast. Thus, the bucky embodiment also may initially compress the posterior breast tissue at the chest wall sufficiently to stabilize this breast tissue against displacement laterally toward the chest wall and from the imaging area both initially and subsequently as the bucky assembly's inclined surface pushes upwardly the underside of the middle and anterior breast portions.

In accordance with one embodiment, the paddle can be converted to and from a flat compression paddle to a conforming tilt paddle with release of a holding device as by a simple turning of a knob on the holding device.

In accordance with a paddle embodiment illustrated herein, the paddle has a flat chest wall portion that always remains horizontal and there is gentle transition across a curved plastic hinge section to an inclined or tilted portion that automatically adjusts the tilt angle for maximizing patient comfort by automatically adjusting the tilt angle to each patient's breast shape and density. Preferably, the hinge portion is a continuous bend with a gentle transition from a flat horizontal, posterior surface to the inclined surface which results in better X-ray continuity and comfort. The flexed portion and hinge section automatically adjust the tilt angle to the breast's shape and density to provide more uniform middle and anterior breast compression. Because the breast engaging paddle and hinge are X-ray transparent, the patient can easily observe that the paddle is conforming to her breast.

The illustrated paddle embodiment can be easily retrofitted onto existing mammography machines by replacing the existing flat compression paddle, unlike the paddle disclosed in U.S. Pat. No. 5,506,877. The preferred paddle is easily flexed and biased to move downwardly to provide uniform compression for various sizes and shapes of breasts even if not centered beneath the tilted member. Moreover, this retrofitted paddle can be used in the normal manner of the former flat compression panel which the operator has been used to by locking the inclined member its upper horizontal position; or the paddle can be used as a tilted breast conforming paddle by release of the lock.

Another mode of operation of this paddle is a fixed inclined paddle which is obtained by the operator releasing the flex lock and squeezing the inclined portion to the desired tilt angle and then locking the inclined portion at this tilt angle. In this locked, inclined mode of operation, the select tilt angle will not change during compression of the breast. The preferred mode of operation is to do the initial posterior chest compression first, then release the flex lock; and allow the inclined portion to swing down against the middle and anterior breast. In this preferred mode of operation after imaging, the inclined flexed portion is squeezed by the operator to a horizontal, closed position and locked in this flat closed, horizontal position. Thus, the paddle is ready for the next imaging operation.

BRIEF DESCRIPTION OF THE DRAWINGS

FIG. 1 depicts an isometric view of a compression paddle in accordance with a first embodiment and wherein the paddle is in an initial position over the bucky, and preparatory to compressing the breast to be imaged;

FIG. 2 depicts a view of a standard mammography machine;

FIG. 3, labeled prior art, depicts a view of a prior art rigid horizontally flat compression paddle and parallel bucky;

FIGS. 3A–3E illustrate breast compression and skin displacement using a conventional paddle and bucky of the prior art;

FIGS. 3F–3H illustrate breast compression and skin displacement using embodiments of this invention;

FIG. 4, labeled prior art, depicts a view of a rigid and downwardly angled compression paddle;

FIG. 5, labeled prior art, depicts a view of a rigid compression paddle tiltable at its midpoint;

FIG. 6, labeled prior art, depicts a view of a rigid compression paddle wherein the paddle is hinged to a vertical end wall of a paddle tray;

FIG. 7 is a relatively enlarged side view of the embodiment of the invention shown in FIG. 1;

FIG. 7A is a diagrammatic illustration of a paddle having a plurality of hinge sections to provide multiple flexed, breast compression inclined surfaces;

FIG. 7B is a diagrammatic illustration of a paddle having a continuous, X-ray transparent flex portion bendable over the middle and anterior breast portions to conform more closely to the contour of the breast;

FIG. 8 is an exploded view of the paddle of FIG. 1 to show the mounting of a protective liner and spring mechanism;

FIG. 9 depicts the spring mechanism of FIG. 8 that is used in this first embodiment to provide an adjustable force to the movable section of the inventive paddle;

FIG. 10 is a perspective view of a paddle according to a second embodiment of the invention;

FIG. 10A is a perspective view of the second paddle embodiment shown in the open position;

FIG. 10B is a rear, perspective view of the paddle shown in FIG. 10A;

FIG. 10C is a side-elevational view of the paddle shown in FIG. 10;

FIG. 10D is a side-elevational view of the paddle in its open position;

FIG. 10G is a side-elevational view of a biasing means and of the flex lock;

FIG. 10H is an enlarged view of the biasing means and flex lock;

FIG. 18 is a sketch of an alternative embodiment of the invention wherein the bucky surface that supports the breast is contoured;

FIG. 19 shows an embodiment of the invention wherein the bucky is contoured and the compression paddle includes a flexing compression surface shown in a tilted position;

FIG. 20 shows the embodiment of FIG. 19 wherein the flexing portion of the paddle of FIG. 19 is shown in a closed or un-tilted position;

FIG. 22B shows the bucky of FIG. 22A in a tilted mode to function similarly as the tiltable bucky of FIGS. 14 and 15;

FIG. 23 is a diagrammatic view of a tiltable bucky cover and a conventional paddle;

FIG. 24 illustrates a combination of a tiltable bucky and the hinged paddle of FIG. 1 and FIGS. 10–10J;

DETAILED DESCRIPTION OF THE PREFERRED EMBODIMENT

Figure 3C:
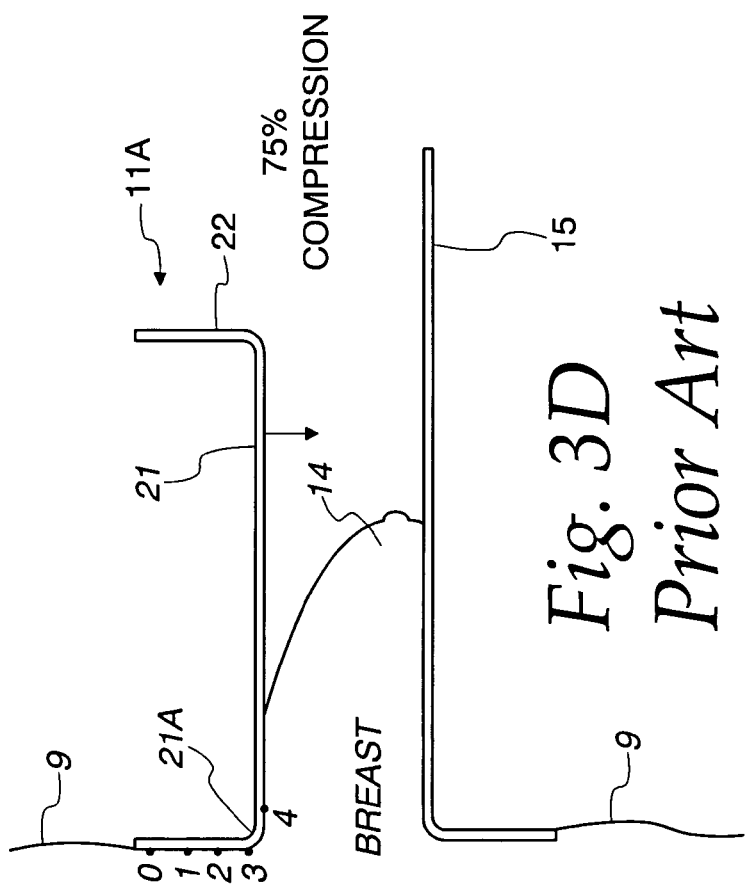
Figure 3D:
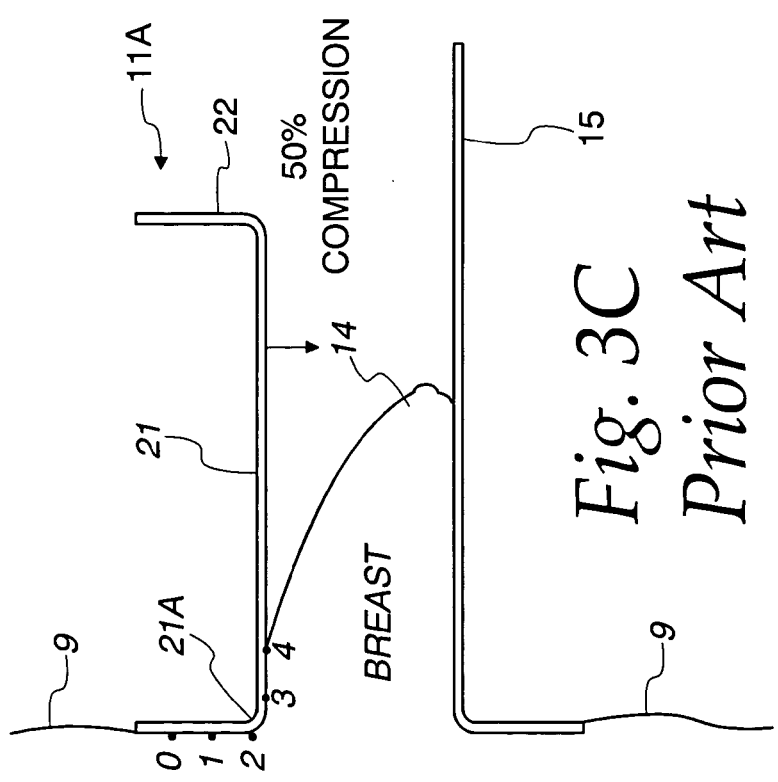
Figure 3F:
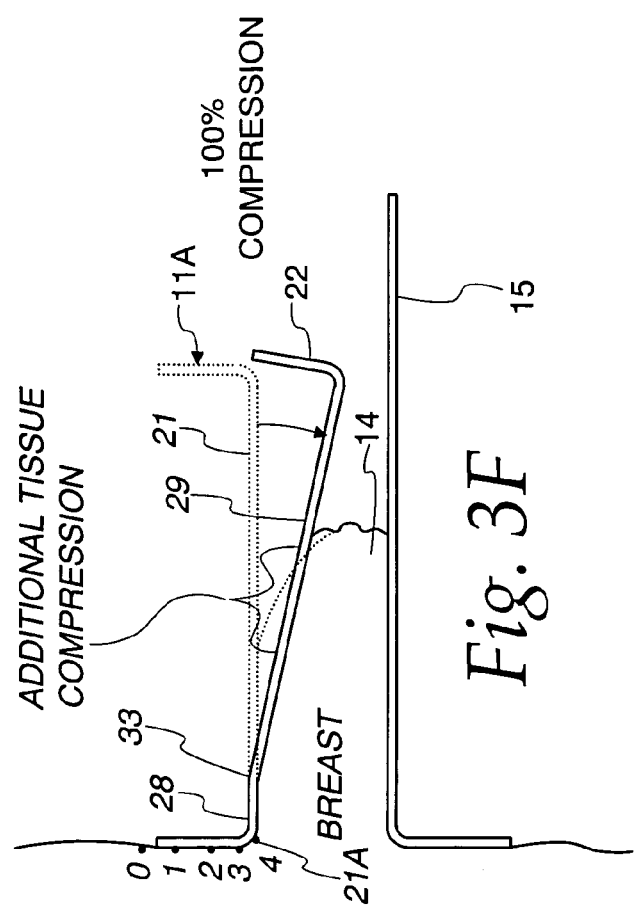
Figure 3E:
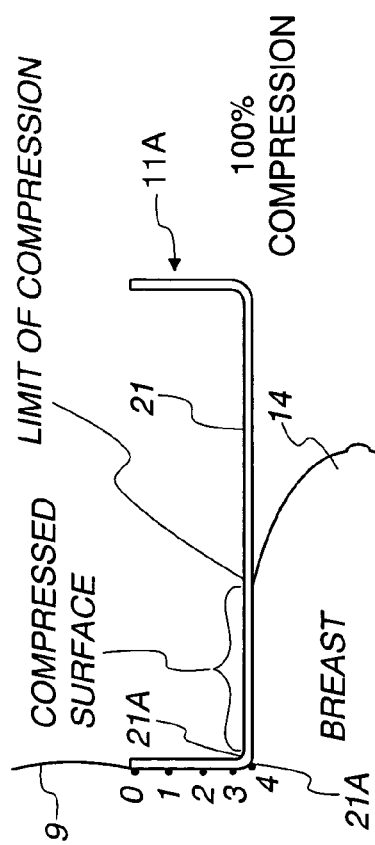

Referring to FIG. 1 that shows a breast compression device or paddle 11 for use in a common type of mammography imaging machine 12 (FIG. 2) with which the invention paddle can be utilized. In the procedure for taking a mammography image, the patient's breast is supported on a support plate or bucky 15 holding an X-ray detector such as a film in a film cassette 16. An X-ray source 17 provides the X-ray s to take an image of the breast. The X-ray beam indicated by arrow lines 19 covers the X-ray film 16. One edge of X-ray beam extends essentially parallel to the patient's chest and it and other incident X-ray s encompass the breast and the area of film 16. A compression paddle 11A is positioned adjacent the chest wall and over the breast 14 preparatory to compressing the breast for taking an X-ray image of the breast.

The compression paddle 11 shown in FIG. 1 is preferably constructed of a radiolucent or X-ray transparent material such as PETG (polyethylene terephtalate glycol) plastic that is 0.075 to 0.095 inches thick. The PETG material is radiation or X-ray transmissive so as to minimally impede the X-ray beam 19 which is transmitted from by source 17 (see FIG. 2). The paddle 11 is also transparent to the human eye to allow the technologist who is performing the mammogram to visually confirm the position of the breast prior to the exposure and for the patient to observe the breast compression.

The illustrative paddle 11 is rectangular and tray-like in appearance, i.e., it is an open top surface, a bottom surface 21 comprising sections 28 and 29 (as will be explained herein below), and a peripheral side wall generally labeled 22. The side wall 22 is mounted to a yoke 23 along three of its sides 22A, 22B, 22D by suitable bolts 25. Yoke 23 extends along the outside of the rectangular wall 22. The yoke 23, in turn, is adjustably mounted on machine 12, as is known. The various corners of the side wall 22 are all beveled for protection of the patient from scratches or abrasions. The paddle 11 can be retrofitted to existing mammographic machines by simply attaching the yoke to existing machines in the manner that the conventional paddle was attached.

Refer now also to FIG. 7. Importantly, the bottom or breast engaging surface 21 comprises a first posterior section 28 and a second section 29 having an inclined surface. Posterior section 28 is about one inch in width and is positioned adjacent the chest wall of the patient. (Note, the orientation of FIGS. 1 and 7 are reversed relative to one another.) As paddle 11 is moved downwardly to compress the breast, the posterior section 28 tends to push the breast 14 downwardly, rather than to force the breast toward or into the breast wall, as occurs when using the prior art paddle without an inclined portion.

The lower surface 21 of paddle 11 comprises a posterior section 28 and a movable or "flex" or inclinable section 29. Preferably, the posterior section is flat, horizontal and rigid and the tilt section is joined to the posterior section by a bendable or flexible hinge portion 33 that bends smoothly or "flexes" about an elongated band of material of selected width, as indicated in FIG. 7. Band 33 is located between the sections 28 and 29 and the flexing or bending of the section 29 is substantially parallel to the patient's breast. The posterior section 28 is thus not pivotable along a pivot or hinge line, but rather the flex section 29 flexes and smoothly bends at about one quarter inch (¼") width (See 33 in FIG. 7) that extends across the bottom surface 21.

The preferred and illustrated hinge is X-ray transparent and is preferably a living hinge of integral plastic that does not show on the X-ray image of the breast. Also, the vertical front wall 22c of the paddle does not project onto the image of the breast unlike the prior art paddle that is pivoted at its center as disclosed in an above-mentioned patent. While a single hinge or hinge band 33 of about ¼ inch is used in the preferred embodiment illustrated in FIGS. 10–10I, it is to be understood that multiple hinges or hinge bands 33 and 33a may be used, as illustrated in FIG. 7A. In the FIG. 7A embodiment, the first hinge band or flex point 33 is located, as above described, adjacent the chest wall. The second hinge band or flex point 33a is located outwardly of the flex point 33, e.g., at about the juncture of the middle and anterior breast portions to provide a first inclined bottom paddle surface 21x over the posterior and middle breast portions and a second inclined bottom paddle surface 21y over the anterior breast portion and having a greater inclination to the horizontal than the middle breast compression surface 21x. Thus, it will be seen that breast compression surface 21 at the bottom of the paddle may be formed with several flat rigid portions joined by several flexible hinge points to have the paddle conform more closely to the shape of the middle and anterior breast portions. The number of hinge points may be more than one or two hinge points illustrated herein. Alternatively, to having multiple hinge points as described in connection with FIG. 7A, the X-ray transparent living hinge band may start at adjacent the chest wall (FIG. 7B) and extend continuously over a wide area such as over the middle and anterior breast portions as illustrated by the flexible, continuous wide band 21z in FIG. 7B. The flexible wide band 21z will allow conforming to the breast middle and anterior portions. In the FIGS. 7A and 7B embodiments, a biasing spring, as discussed above in connection with FIGS. 1–9 or, as discussed hereafter in connection with the FIG. 10 embodiment, will apply to compress force to breast compression surfaces 21x and 21y in FIG. 7A or to the continuous flexible surface 21z in FIG. 7B. In the embodiments of FIGS. 7A and 7B, it is preferred to lower the paddle along the chest wall for about 4 to 6 centimeters to compress the posterior breast portion which is adjacent the chest wall and then to release the flex portion 29 having two hinged surfaces 21x and 21y or the continuous flex surface 21z to further compress the middle and anterior breast portions. That is, it is preferred to have the paddle surfaces 21x and 21y or paddle surface 212 in a horizontal plane over an initial compression distanced 4 to 6 centimeters descent of the paddle before releasing the paddle surfaces 21x and 21y or 21z to move further downwardly under a biasing force to move into positions, respectively, shown in FIGS. 7A and 7B.

The most commonly used paddle 11a and bucky 15 are shown diagrammatically in FIG. 3 where the paddle 11A is a rigid plastic paddle in the shape of a tray having an open top, a flat horizontal rigid bottom compression surface 21 and upstanding, peripheral side walls 22. In operation, the operator pushes the patient's chest wall 9 tightly into the machine, as seen in FIG. 3A, in order to compress the posterior breast tissue adjacent the chest wall, because this posterior tissue is most likely to contain lesions, if any are present in the breast, and because this posterior tissue is closest to the lymph nodes. The discomfiture felt by the patient when using the compression paddle of FIG. 3A is due to the large displacement of the inner, posterior corner 21a of the compression paddle 11a as it travels downward and displaces the breast skin to the left as viewed in FIGS. 3A–3H. Equally spaced points 1, 2, 3, 4, 5 and 6 and have been marked on the top skin of the posterior and middle breast portions. The breast changes its shape as the flat, horizontal bottom compression surface descends and flattens the breast. The breast tissue compresses and displaces the kin being engaged by the paddle adjacent the posterior corner 21a and does not stretch but is displaced to the left. That is, each of the points 1, 2, 3, etc. the skin must be displaced to the left of the substantially vertical plane of the chest wall from its original position.

As the paddle corner 21a travels down along the chest wall 9 from the zero percent (0%) compression of FIG. 3A to the twenty-five percent (25%) compression of FIG. 3B, the skin at point 1 is displaced horizontally to the left as seen in FIG. 3B to the plane of the chest wall. As the paddle corner descends to fifty percent (50%) compression, as shown in FIG. 3C, the skin at point 2 has to be displaced to the plane at the chest wall which is a larger leftward displacement than the leftward displacement than the skin at point 1 was displaced at the twenty-five percent (25%) compression. As the paddle descends further, the skin point 3 (FIG. 3D) will displace even further to the left than either skin points 1 or 2 to reach the chest wall. When there is a hundred percent (100%) compression (FIG. 3E) of the posterior breast, the paddle corner will have already pulled the skin taut with large displacement of point 4 into the chest wall. If the paddle has descended to where the skin is taut and the tissue is not shifting because the posterior breast tissue is compressed and the paddle corner tries to stretch the skin further to shift point 5 on the skin into the plane adjacent the chest wall and/or to shift Point 6 on the skin into the chest wall plane the friction between the skin and the bottom paddle becomes too large and holds the skin against shifting into the plane of the chest wall, and then, in many instances, pain and discomfiture will be felt as the skin is experiencing forces that will try to tear it. It is this attempt to tear the skin or an actual tearing of the skin that is so discomforting to the patient. The pain is from trying to stretch and to tear the skin being held by friction at the bottom of the paddle rather than from further compression of the breast.

By way of example only, when using the parallel paddle and buckey prior art arrangement, a paddle downward travel of 4 to 6 centimeters would, in many instances, be sufficient to compress the posterior tissue sufficiently for good imaging and an additional 3 centimeters downward was done in order to compress the anterior breast sufficiently for good imaging of the anterior breast. Often the discomfiture due to trying to stretch the skin occurs in this last 2 to 3 centimeters or so as the skin under the paddle at points 5 and 6 is held by friction between the paddle and compressed breast from displacing into the plane of the chest wall. Sometimes, the patient could not bear the pain over these last few centimeters of paddle travel, and the operator stopped the paddle descent without obtaining a good compression of the anterior breast. In the present invention, if the paddle travels downwardly and through 4 to 6 centimeters and achieves the necessary good posterior breast compression from the paddle section 28 at the chest wall, the paddle section 28 need not be displaced downwardly for another three centimeters to compress the anterior breast because the inclined portion 29 can be swung down to compress the anterior breast without the horizontal paddle section being lowered these few additional centimeters. Alternatively, after the initial compression of 4 to 6 centimeters in this instance, the inclinable portion of the bucky assembly may be pivoted to compress the middle and anterior breast without further displacement of skin and tissue at the chest wall. While a few centimeters does not seem to be a great distance, such a further displacement will have a great effect, in many instances between little or no discomfiture and a lot of pain and discomfiture.

In order to provide a hinge portion 33 for flexing or bending that provides minimal stress to the bottom surface 21 or the side walls 22, an aperture 20 (as clearly shown in FIG. 7) is provided in side walls 22B and 22D at area of band 33. The aperture 20 includes a side of about one quarter inch (¼")in length on the bottom surface 21. The aperture 20 is of smooth rounded configuration to minimize the stress on the plastic material. It has been found that a slit or sharp corner is formed on the plastic material, walls 22B and 22D are highly stressed by the flexing action. Aperture 20 permits a significant portion of side walls 22B and 22D to retain sufficient material mass to provide the needed strength to the thin (0.75–0.95 inch thick) plastic material of section 29 for the compressive force required. A force of up to 25 to 37 pounds is typically applied by the posterior section to the posterior breast tissue.

Referring again to FIG. 1 that shows the paddle 11 in a breast compression mode or position. The section 28 pushes the breast vertically downwardly, to provide a compression adjacent the patient's chest wall. As mentioned above, inclined portion 29 flexes along a band 33 that is spaced from the patient's chest. Upon the application of downward force to paddle 11, section 28 will engage and push the breast downwardly. The downward angle of the movable section 29 of paddle 11 is controlled and adjusted, as will now be explained below. Note that a gap or space 20a extends from aperture 20 along side walls 22B and 22D. The function of gap 20A is to prevent any pinching of the breast as the flex section 29 moves. As best seen in FIG. 7, the rigid portion of wall 22A (farthest from the chest and breast) extends downwardly to abut against the flex portion of wall 22A along line 34.

Refer now to FIGS. 8 and 9. As shown in FIG. 9, a spring mechanism 40 and adjustable cam 43 provide a controlled force to push (force) flex inclined or flex portion 29 downwardly about band 33, as indicated in FIGS. 1 and 7. The spring 40 is adjustable to open the angle to about 13° to 15° such as by adjustment of the cam 43, indicated in FIG. 8. The moveable section is molded to be in an open position of about 7° downwardly from the horizontal surface 28, hence the material has to move up or down about 8° to provide a change of 15°, thus minimizing the stress on the PETG plastic. The initial first force usually 25 to 37 pounds to be applied to the breast is provided by the machine 12. The second force to be applied by flex, inclined member 29 is then adjusted by the spring mechanism 40 and is usually in the range of 10–15 pounds of force.

The effect of this two step compression is to spread out and firm the breast tissue near the middle and anterior portion of the breast, which results in improved compression and results in improved visibility of detail. The paddle 11 thus provides a means of providing essentially two complementary forces for compressing the breast. A first force is provided by the posterior section 28 of the lower surface 21 against the firmer chest muscle or tissue and posterior breast tissue, and a second adjustable force is provided by the angled section 29 against the usually smaller, softer and more pliable tissue of the middle and anterior portions of the breast.

Note that the bending action of section 29 is accomplished without the front or chest end of paddle 11 being located in the breast imaging area of the X-ray beam path indicated by line 19, in FIG. 1. This is in full accord with the Federal Mammography Quality Standards Act that state that the shadow of the vertical edge of the compression paddle shall not be visible on the image.

This wide, X-ray transparent hinge extending across the width of the paddle 33, provides a gentle transition between the horizontal posterior section 28 and the inclined section that allows better conformation to the breast irrespective of its shape, size or density and does not provide a shadow on the breast image.

The substantial posterior compression acts to spread superimposed lesions or portions thereof that are adjacent the chest wall without pushing them toward the ribs and from the imaging area.

FIG. 8 is an exploded view of paddle showing the positioning of a U-shaped liner 35 mounted within the inner surface of walls 22A, 22B and 22D. The liner 35, in conjunction with the gap 20A, functions as a protective mechanism to prevent pinching of the patient, such as when the paddle 11 is used to take a side view of the breast. The liner 35 inhibits any patient's skin from being caught between the flexing portion and the rigid portion of sidewall 22; and the gap 20A, further assures the rigid and flex portions do not press together. The liner 35 is U-shaped and fits closely within the inner surface of sidewall 22 with the bight of the U-shape adjacent the side positioned against the patient's breast. The liner 35 is pivotably affixed at points 37 on the rigid section 28.

A biasing spring 40 (See FIG. 9) formed as two connected U-shape heavy wires is mounted in a recess 42 formed on the liner 35. That is, the bottom length 44 of spring 40 is suitably clamped in recess 42 (See FIG. 8) formed along the bottom edge of liner 35. A selected force is applied to the upper side 41 of spring 40 by a suitably known cam 43. Cam 43 may be manually adjusted to provide a low force wherein the flex section 29 is in position A in FIG. 7, or a high force wherein the flex section 29 is in position B in FIG. 7. It has been found that some technicians prefer to have the flex section 29 in the open or fully flexed position (See FIG. 1) as the mammography procedure initiated; other technicians prefer to have the flex section 29 in the closed position (See FIG. 8) at the initiation of the procedure. Either practice appears suitable.

In operation, as force is applied to spring 40, the spring transmits this force to the liner 35 to flex and adjust inclined member 29 to provide a selected, controllable, and easily adjustable manner.

Figure 10E:
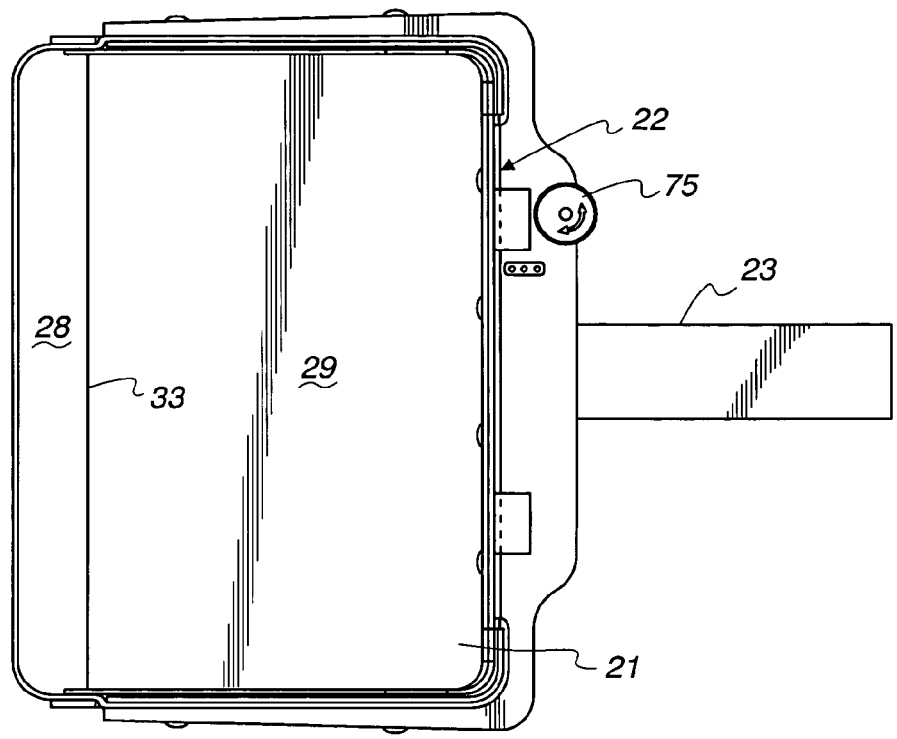
FIG. 10E is a plan view of the paddle shown in FIG. 10.
Figure 10F:
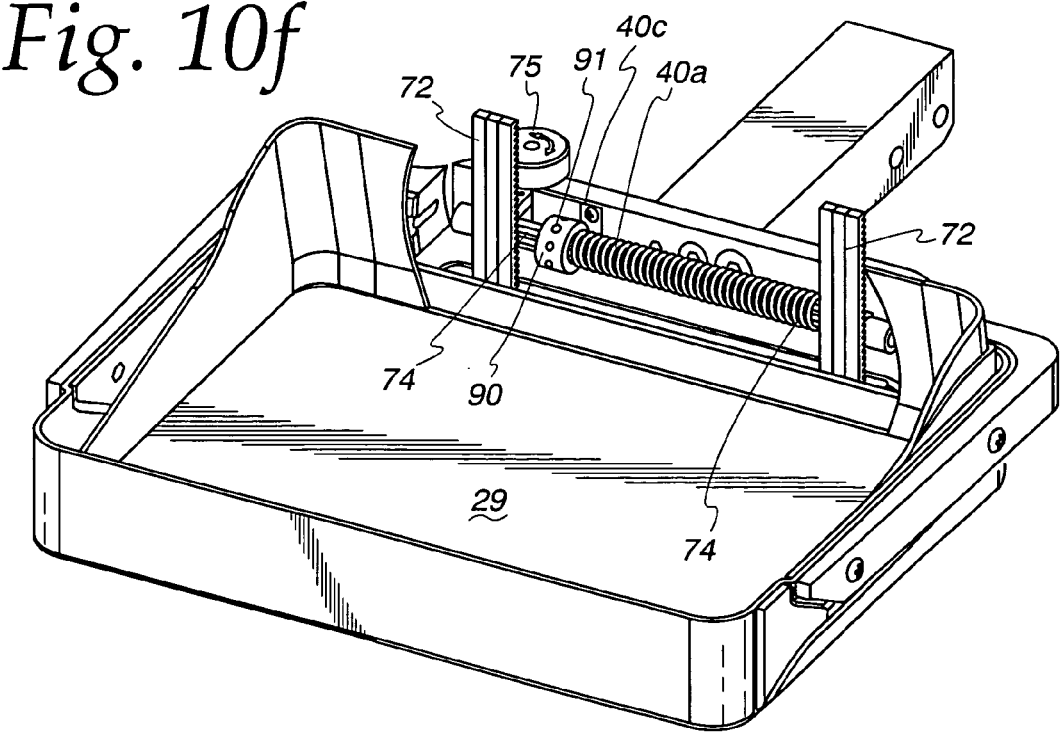
FIG. 10F is a perspective view of a paddle with a broken away wall showing a torsion biasing spring for the flex portion of the paddle and a flex lock therefor.
Figure 10I:
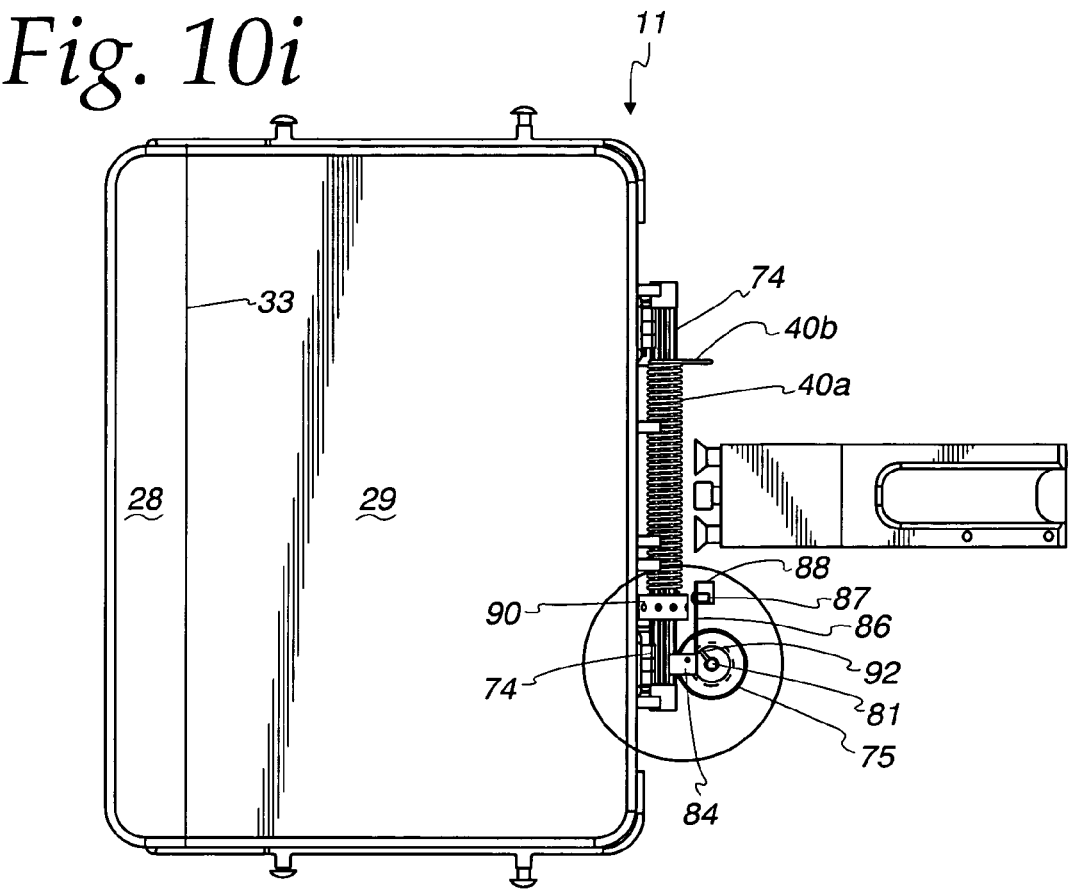
FIG. 10I is a plan view which is broken away to expose the biasing means and flex lock.

In accordance with a further embodiment of the paddle illustrated in FIGS. 10–10I, the spring for biasing the flex section 29 downwardly about the living hinge 33 comprises an elongated torsion spring 40a (FIG. 10F) which has one end for biasing the anterior end of the flex section and opposite end fixed to the paddle frame. The torsion spring encircles an elongated shaft 71 and an elongated pinion (FIG. 10G).

The flex section is guided for vertical and even pressure across the breast, if the breast is centered or not centered under the flex inclined portion 29 by a pair of spaced guides 70 that do not bind when the breast compression is not centered under the flex section. The guides assure a level surface across the width of the breast and allows breasts of different sizes and shapes to be positioned off-center and still be properly compressed and imaged. Herein, the illustrated guides 70 are in the form of vertically-extending racks 72 engaged with the pinion 74(FIG. 10H) with the pinion mounted for rotation about the shaft 71. The racks 72 have their respective lower ends fixed to an outer side member 76 (FIGS. 10D and 10G) of the flexed section 29 opposite the hinge 33 at the other side of the flexed section. The upper ends of the racks are housed with a pair of tower shaped housings 80 that are fixed to the tray frame. As the inclined flex section 29 shifts towards its upper closed position the upper ends of the racks 72 raised within the tower shaped housings 80. The racks are meshed with the pinion and as the racks travel upwardly, they rotate the pinion about the shaft and twist the torsion spring 40a to store energy therein. When the lock is released with the inclined section 29 in its upper closed position, the torsion spring turns the pinion and the pinion drives the racks downwardly to apply the desire compression force of 10 to 15 pounds to the anterior and middle breast portions. When the section 29 is manually squeezed from its open position of FIG. 10 to its closed position of FIG. 10C, then the racks shifts upwardly and the pinion 74 in the direction to wind the torsion spring and to store more energy therein.

The torsion spring 40a has a first fixed end 40b (FIG. 10G) fixed to the outer frame of the paddle 11 and the other end 40c (FIG. 10F) of the torsion spring 40a is fixed in a hole of a rotatable disc or wheel 90 which is rotatable mounted on the rack to rotate thereabout. The disc has a circumferential surface with a plurality of holes 91 therein to receive the end of a tool. The disc 90 is locked to the pinion by a set screw until it is desired to change the biasing force of the torsion spring 40a. To increase the biasing force, the set screw is released and the tool is inserted into the disc 90 and the disc is turned in a direction to wind the coils of the torsion tighter and then the set screw is turned into the pinion to lock the disc to the pinion. The pinion 74 freely rotates about the supporting shaft 71 and has its opposite ends engaged with the respective left and right racks 72. The newly increased biasing force is thus imparted by the pinion to these racks and thereby to the flex portion 29 fixed to an guided by the rack ends. As stated above, the racks guide the flex portion 29 to apply the compression force to the breast from the biasing spring whether the breast is centered on the centerline or is close to one or the other of the left or right hand racks.

Ths illustrated lock shown in FIGS. 10G and 10H comprises a rotatable knob 75, which is mounted to an upper end of a shaft 81 which is rotatable clockwise to carry a lock pin 82 to move into engagement with teeth and pinion 74 to lock the pinion against turning against turning under the urging of the torsion spring 40a. Because the pinion is held from rotation by the lock pin therein, the engaged racks cannot move downwardly.

The lock may be applied when the inclined section is closed as seen in FIG. 10 such that the paddle operates in a parallel mode of a conventional paddle now used by most people. The lock may be applied when the inclined section 29 is fully open and inclined downwardly as seen in FIGS. 10 and 10B to provide an inclined section locked in a predetermined position to act as a rigid inclined panel movable to engage the middle and anterior portions of the breast to apply a compressive force to the middle and anterior portions of the breast if it were desired to do so. A third mode of operation is the usual one in which the knob 75 is turned to lock the flex section 29 in an aligned position in which is aligned horizontally with the rigid, posterior position 28 of the paddle. A first compressive force usually in the range of 20 to 40 pounds.

Figure 10J:
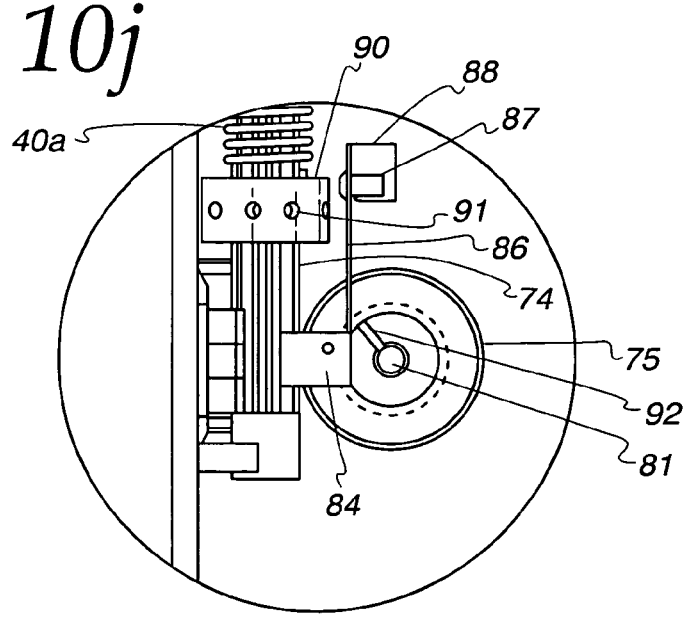
FIG. 10J is an enlarged view of the flex lock shown in FIG. 10I.

The lock of the embodiment illustrated in FIGS. 10I and 10J comprises a toothed locking block or detent member 84 having teeth that are selectively moved into engagement with the teeth of the pinion 74 to hold the pinion 74 against turning under the urging of the biasing force or moved from engagement with the teeth of the pinion 74 to allow the pinion to rotate under the urging of the biasing force or moved from engagement with the teeth of the pinion 74 to allow the pinion to rotate under the urging of the biasing force the spring 40a to lower the racks 72 and the flexed section 29 to compress the breast. Herein, the toothed locking member 84 is mounted on the free end of a leaf spring 86 that has its opposite end secured by a fastener 87 to a fixed portion 88 of the paddle frame. The leaf spring in its unbiased position holds the toothed locking member 84 spaced from the pinion and in an unlocked position. To shift from this unlocked position to the lock position, the knob 75 and its shaft 81 are turned to bend the leaf spring 86 and to move the toothed member 84 into engagement with the teeth of the pinion. Herein, a cam in the form of a horizontally extending pin 92 is fixedly mounted on the shaft 81 and when turned counterclockwise, as viewed in FIGS. 10I and 10J, pushes the leaf spring to bend and to move the toothed locking member into locking engagement with the pinion. When the knob 78, shaft 81 and pin 92 are rotated clockwise, the pin disengages from the leaf spring which then returns to its unflexed condition and carried the toothed locking member to be spaced from the pinion so that the pinion is free to rotate to lower the racks and the flex section to compress the breast. The leaf spring is vertically oriented to bend toward or from the pinion, but does not bend vertically under the urging of torsion spring 40a being applied through the pinion and toothed member 84 to the leaf spring. Thus, the lock may be applied or released with a single timing of the actuator 74.

Figure 25:
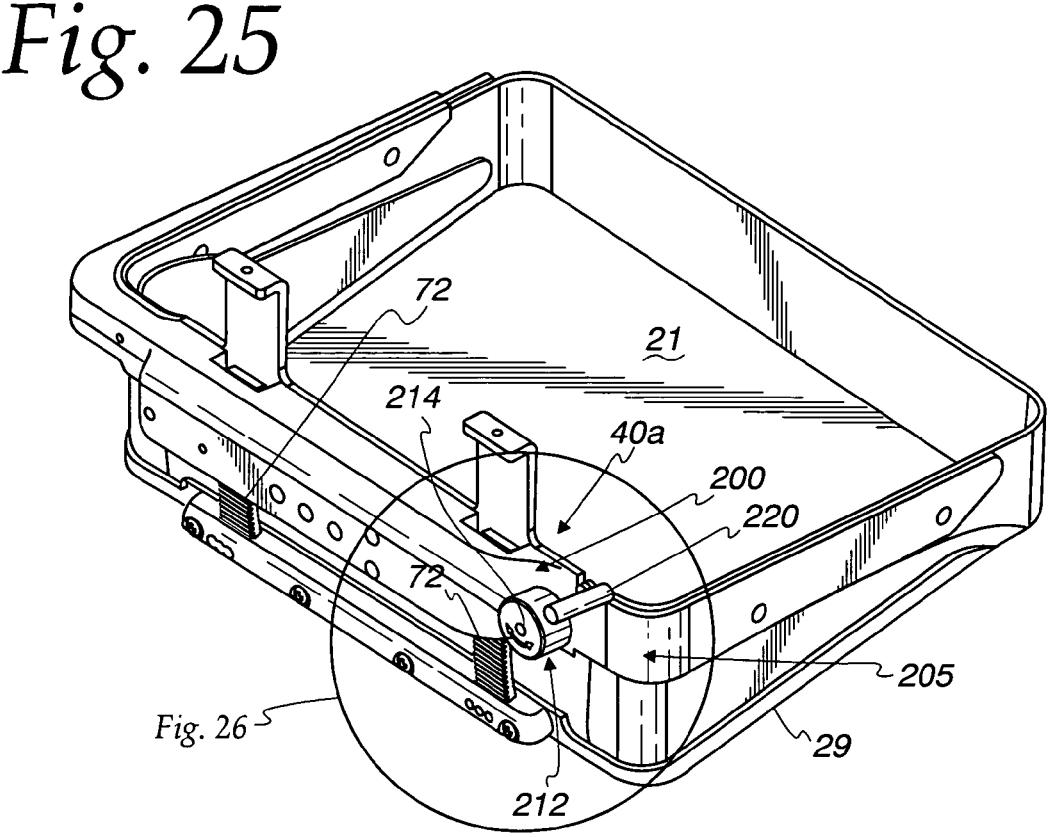
FIG. 25 is a perspective view of a brake disc for locking and releasing the flexible section of the paddle in accordance with an embodiment.
Figure 26:
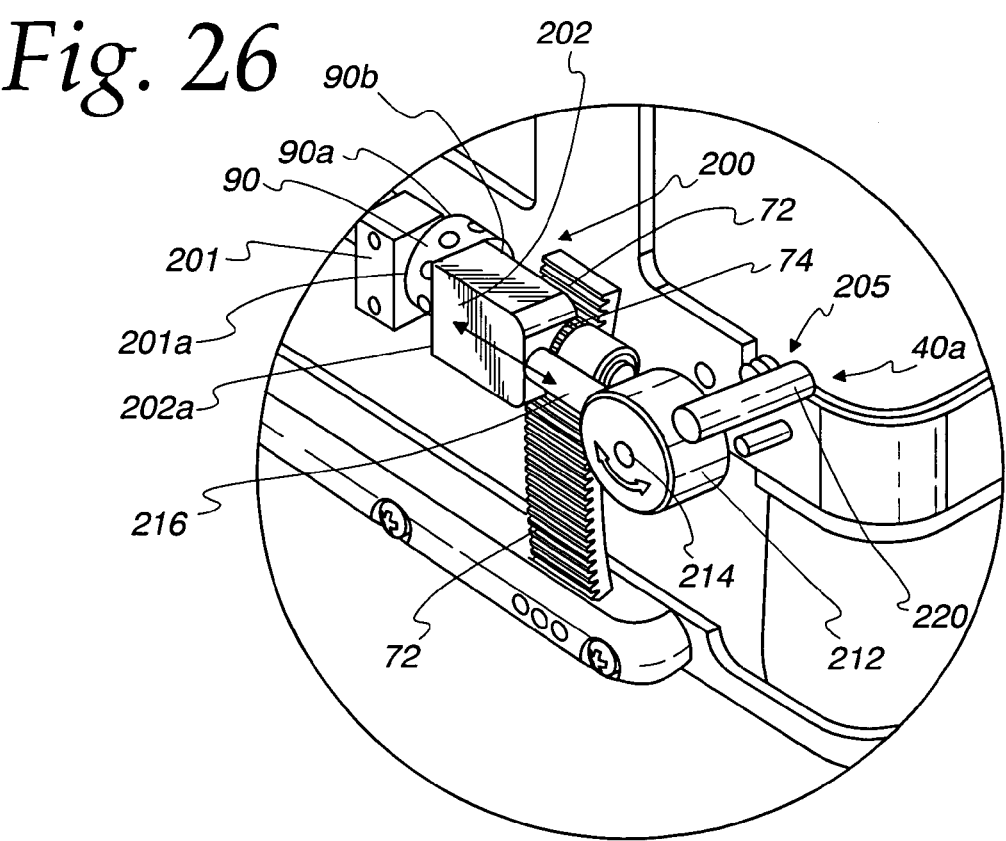
FIG. 26 is an enlarged, exposed perspective view of a brake disc lock in accordance with the embodiment of FIG. 25.

In an embodiment illustrated in FIGS. 25 and 26, the holding device or lock 40 or 40a for holding the flexed paddle section 29 in a particular position such as an upper horizontal position or in an inclined lowered position may be in the form of a selectively operated friction brake device 200 (FIGS. 25 and 26) having a pair of brake pads 201 and 202 on opposite sides of a rotatable brake disc 90 mounted on the pinion 74 and connected by the racks 72 to the hinged section 29. A turning of an actuator 205 in one direction, counterclockwise in FIGS. 25 and 26, causes the brake pads 201 and 202 to frictionally engage opposite sides of the disc 90 located therebetween and thereby lock the disc 90 and connected paddle section 29 against movement. To release the brake, the actuator 205 is turned in the opposite direction to shift the brake pads 201 and 202 from holding engagement with the disc 90 to allow the flexible section 29 to shift under the biasing force being applied thereto.

In the disc brake embodiment shown in FIG. 26, the left hand brake pad 201 is fixed to the frame of the paddle and has a right, vertical brake surface 201a disposed in facing relationship to a left vertical sidewall 90a on the disc 90. The slidable brake pad 202 is mounted for sliding horizontal movement on the paddle frame and has a left vertical brake surface 202a to engage the right vertical face 90b of the disc 90. The disc 90 has an internal gear tooth surface meshed with the gear teeth of the pinion 74 to turn therewith but the disc may slide to the left or to the right on the pinion and the disc is pushed into the fixed brake pad face 201a by the slide brake pad face 202a when the actuator 205 is turned counterclockwise as viewed in FIG. 26.

The illustrated actuator 205 comprises an eccentric cam wheel 212 mounted to turn about a horizontal shaft 214 to move its peripheral eccentric surface 215 against a cam follower in the form of a horizontally extending shaft 216 fixed to and slidable with the movable brake pad 202. A cam wheel lever 220 extends upwardly from the eccentric cam wheel for turning the cam wheel 212 about its mounting shaft 214 to push the slidable brake disc to slide the disc 90 on the pinion into braking engagement with the fixed brake pad 201. A turning of the lever 220 counterclockwise causes a braking and/or locking. A turning of the lever 220 in the clockwise direction releases the brake. The operator will develop a feel for releasing the brake slowly to allow a slipping as a slip clutch between the disc and the brake pad surfaces 201a and 202a so that flexed portion 29 is slowly allowed to compress the breast rather than a full, quick release of the flexed section 29 against the breast.

This friction brake device locks the swinging flex section 29 in the horizontal initial position and the knob can be turned incrementally to slowly decrease the friction force until the brake pad surfaces 201 and 202 slip relative to the brake member 203 so that inclined section 29 may be slowly lowered to compress gradually the middle and anterior breast portions. This avoids a sudden application of the full force of flexed section 29 against the breast. Further, this avoids the noise that is sometimes heard in the release or application of the locking device described in connection with FIGS. 10–10I.

Figure 13:
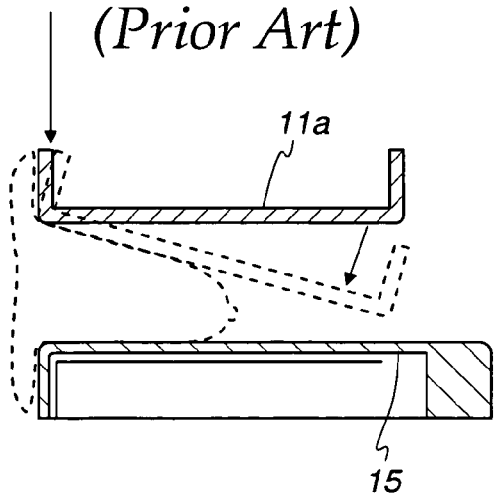
FIG. 13 is a sketch of a prior art paddle that is tiltable.

In devices such as depicted in the prior art, as depicted in FIG. 13, the compression paddle is rigid, and the forces are normally non-uniform along the breast, with the most compressive force being applied closest to the chest wall and the least compressive force towards the nipple where the breast is relatively smaller and thinner.

Figure 14:
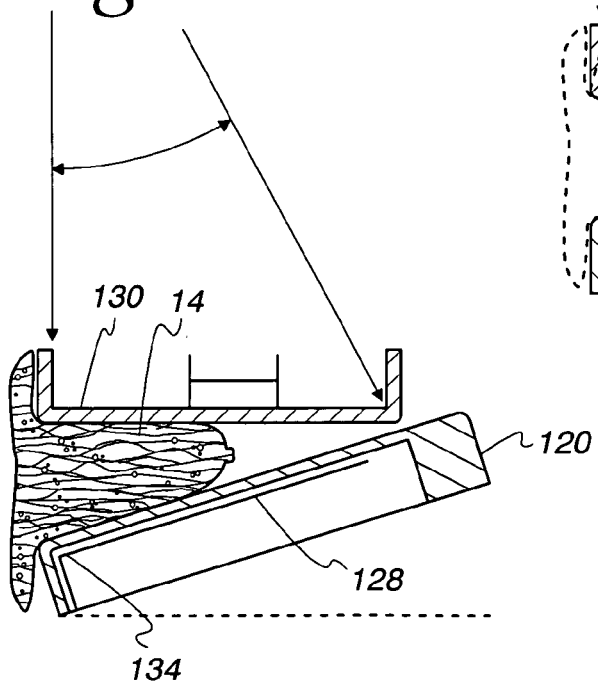
FIG. 14 diagrammatically illustrates the bucky being tiltable which results in a number of advantages as will be described herein below.

An alleged improvement to the cited problem is disclosed in the prior art as depicted in FIG. 14 wherein the lower surface while rigid, is angled downwardly to more closely conform to the upper surface of the human breast. In this prior art, the downwardly angled rigid surface may be suitable for one type and size of breast, but may be completely unsuitable for other types or sizes of breast and its angled surface is not adjustable, other than vertically.

Figure 15:
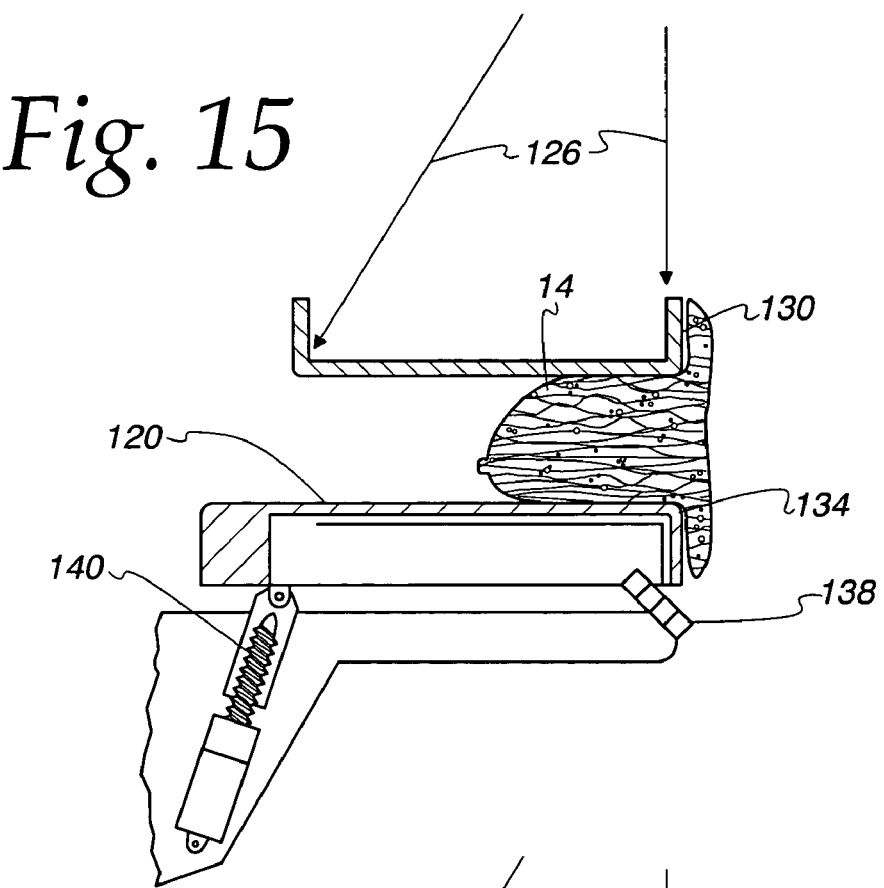
FIG. 15 shows a mechanism for tilting the bucky (in this view the mechanism is in a rest or non-activated mode.

Another type of pivoting compression paddle is depicted in FIG. 15, wherein the paddle is pivoted at its center to permit the paddle to be angled to conform to the contour of the breast once the paddle makes contact with the patient's breast. This causes the paddle to angle downwardly to obtain compression of the breast. The compression force (and pivoting action) is controlled by spring means. As indicated, by the vertical dotted lines in FIG. 15, when the paddle is tilted it causes the end of the paddle to interfere and occludes the X-ray beam. Also, the pivoting action of the paddle, tends to cause the flesh of the breast to be pushed inwardly toward the chest and blur or occlude the image. This is quite critical since a high percentage of the lesions or trauma is found in the area of the breast closest to the patient's chest.

Figure 16:
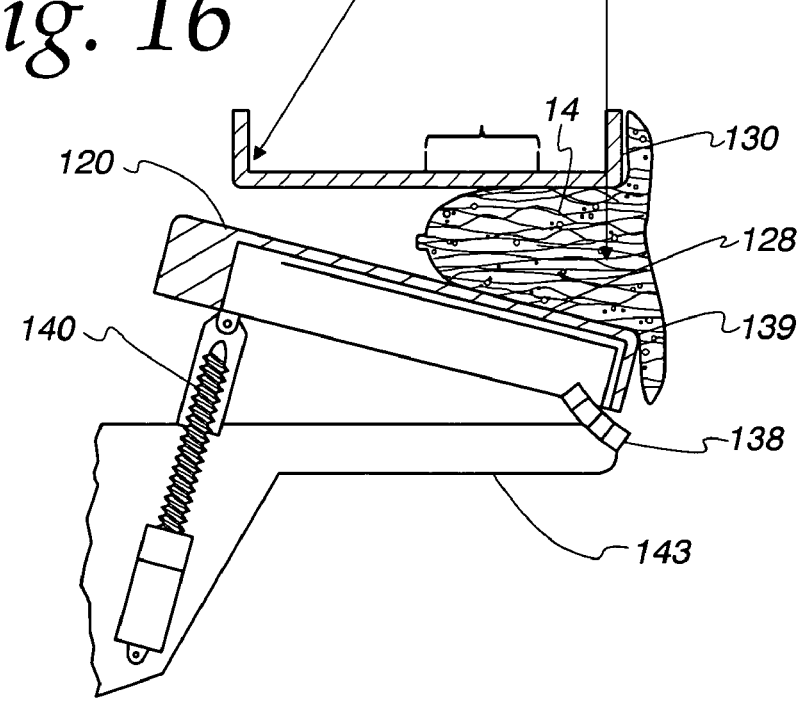
FIG. 16 shows the mechanism wherein the tilting mechanism shown in FIG. 15 has been activated to tilt the bucky.

A modification to the structure of FIG. 15 is depicted in FIG. 16 wherein a lower surface of the compression paddle is shown as being hinged along the lower back corner of the paddle to permit the lower surface to angle downwardly to engage the breast more evenly. The hinge of FIG. 16 appears to be theoretically suitable. However, forming a hinge on a thin plastic applicable for mammography purposes is just not practical or suitable, and probably not even feasible (in the present invention a plastic of a thickness of 0.075–0.090 inches is used).

As alluded to above, one of the known drawbacks of the prior art compression paddles as depicted in FIGS. 15 and 16, is that as the paddle is moved downwardly to bear against the breast, the breast tissue near the chest wall tends to be pushed inwardly toward the chest. This tends to occlude and or affect the image taken near the chest wall (wherein a high percentage of the lesions occur). Further, the nipple end of the breast is often not sufficiently compressed so that during imaging, movement of the breast may cause blurring of the image. Basically, in a compression paddle wherein the lower surface is horizontally flat and rigid and is squeezed against a horizontal flat bucky, the breast is not compressed in a uniform manner, and the breast is not compressed into a suitable flattened configuration as desired for mammography purposes.

Figure 11:
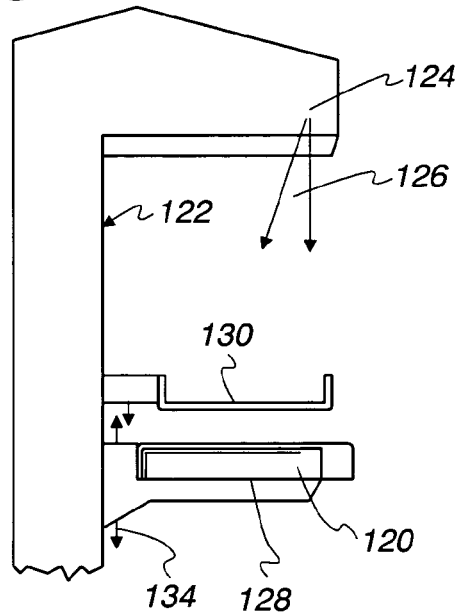
FIG. 11 is a sketch of a mammography machine incorporating the inventive tiltable bucky according to a third embodiment of the invention.
Figure 12:
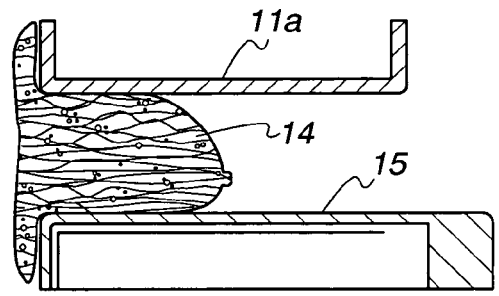
FIG. 12 is a sketch of a prior art type of bucky and compression paddle in relatively enlarged view.

Referring now to another embodiment having a tiltable bucky assembly is shown in FIG. 14. In FIG. 11, the mammography machine or system 122 includes an X-ray source 124 that provides an X-ray field indicated by the lines 126 of beams that extend downwardly to make an image of the breast on known type film or know digital detectors 128. As is known, a direct beam from the X-ray source is parallel to the patient's chest wall adjacent the patient's breast. A compression paddle 130 combines with the tiltable bucky 120 to compress the breast, as will be further described herein. The tiltable bucky is mounted to be moveable vertically as indicated by the arrow lines 132, as is standard. In FIG. 11, the tiltable bucky 120 is shown in a horizontal position; that is, its upper breast compression surface 122 is in a non-tilted position. In normal mammography procedure, this is the position of the bucky to receive the patient's breast, and the bucky is moved up and down to best accommodate the patient. The X-ray field is provided such that beams of the X-ray field 126 are directed to be adjacent and parallel to the chest wall of the patient. If a rigid prior art compression paddle is tilted as disclosed in the above-identified patents, the vertical end wall of the paddle will protrude into the field of the X-rays and occlude the X-rays. Note that in the inventive system of FIGS. 11 and 14, the compression paddle 130 and the hinged area of the bucky provides a sufficiently wide surface engagement with the posterior breast tissue adjacent the chest wall that when they are moved vertically relative to one another, the posterior breast tissue is initially compressed with sufficient force to prevent a later horizontal force component from an inclined portion of the breast pushing the posterior breast tissue toward the chest wall and from the imaging volume. The paddle in FIG. 14 has a posterior vertical end wall but it does not rotate to protrude into the X-ray field 126 as does the vertical wall of the prior art paddle used with a non-rotatable bucky in FIG. 13.

Refer now again to the showing of FIG. 14, the bucky 120 is shown in its tilted position. FIG. 14 also indicates an extended compression of the breast tissue in response to the tilting feature. In FIG. 14, the pivot point 134 for the bucky is beneath the breast, and alongside the film or digital detector 128. In FIG. 14, there is no image occluding paddle end wall or hinge located into the X-ray field or the breast imaging area. Accordingly, the structure of FIG. 14 avoids or prevents any occlusion of the imaging field while obtaining all the advantages of a tilting function.

FIGS. 15 and 16 show details of the structure for providing the bucky tilting function. FIG. 15 shows the bucky 130 in a non-tilted position. In the preferred operation and as the illustrated view of the paddle is first lowered to compress the posterior tissue at the chest wall between the paddle and the stationary bucky and therafter the bucky is tilted to further compress the middle and anterior breast tissue. To this end, a lead screw 140 is suitably mounted, preferably at a slight angle off of the vertical to the back end of the bucky on the bucky support frame 143. The lead screw 140 is controllably driven by a gear motor 142 to move and retain the bucky 130 at a desired position. A concealed utility hinge 138, of any commercially available type, is positioned at the front end of the bucky. Hinge 138 provides a pivoting point 39 that is spaced from the hinge itself by adjusting a hinge slide track within the hinge 138. In one embodiment of the invention, a hinge made by the Soss Company is used. FIG. 16 indicates the movement and positioning of the bucky 120 and the included detector or X-ray film 128. Movement of the bucky 130 from a horizontal plane to an angled position of up to 15% is adequate. A positioning of the bucky at 8% above the horizontal average, and is dependent on the patient's breast anatomy.

Figure 17A:
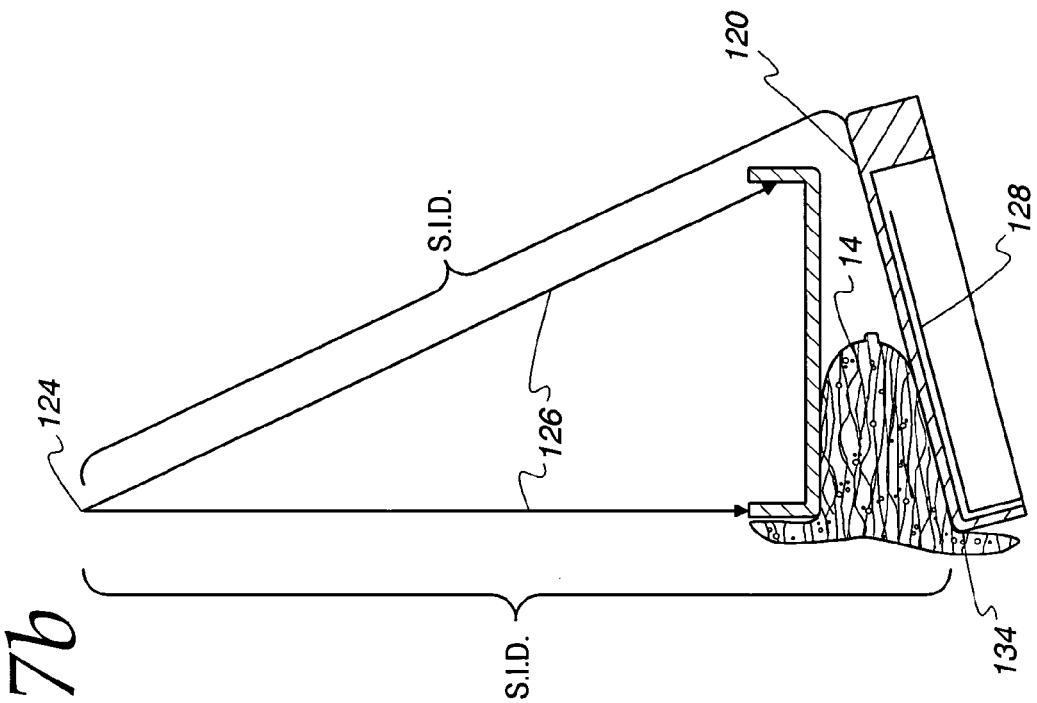
FIGS. 17A and 17B show features of tilting the bucky in accordance with the invention.
Figure 17B:
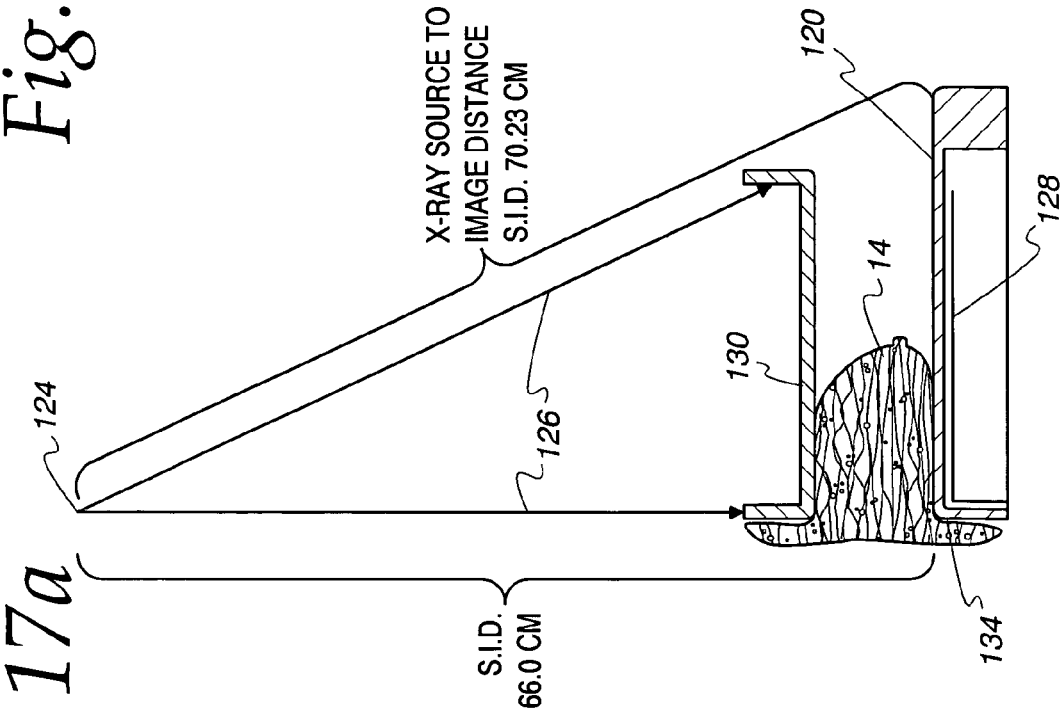

FIGS. 17A and 17B are included herein to show the SID (source to image distance) that may be affected by the tilting bucky. FIG. 17A shows an often used SID of 66.0 cm from one edge of the beam at the chest wall, posterior breast, resulting in a SID of 70.23 cm at the opposite extreme edge of the beam at the anterior breast. The tilting of the bucky assembly and lifting of the X-ray detectors by two or three centimeters substantially reduces the SID at the anterior breast. The long incident rays at the anterior hinge suffer from heel effect which is alleviated by shortening of the SID at the anterior breast.

FIG. 18 shows an alternative embodiment of the inventive bucky labeled 120A wherein the top or breast supporting surface of the bucky is contoured from front to back in a slight or convex curve. The side-to-side lines of the convex surface are straight lines 144. FIGS. 19 and 20 show an embodiment of the invention wherein the bucky 120A of FIG. 18 is used with a unique tilting compression paddle 145. Compression paddle 145 has a complex compression surface comprising a fixed horizontal surface 146, a flex portion 148, and a tilting of portion 150. The horizontal surface 146 of paddle 145 is fixed on a horizontal plane, and is about 2 cm in width and engages the breast adjacent the chest wall with a vertical force. Paddle 145 includes a flexing portion 148 that extends from horizontal surface 146 and bends relative to surface 146. The tilting surface 150 of compression paddle 145 extend from the flexing portion 148. The tilting compression surface is controlled by suitable spring means, not shown, mounted on the paddle support arm to move from the tilted position shown in FIG. 19 to a non-tilted position as shown in FIG. 20. In operation the breast is first placed on and supported in the concave surface on bucky 120A.

The compression paddle 145 in its tilted position as shown in FIG. 19 is caused to lightly engage the breast. The technician next adjusts the breast on the bucky. The compression paddle 146 can next be moved to compress the breast with the surface 146 providing a vertical compressive force, and thereafter the tilting portion can be activated to tilt to the position shown in FIG. 20. Note again, as indicated in FIG. 20, that the additional breast tissue compression is similarly as in FIG. 14. The paddle 145 has all the advantage of being tiltable, and it avoids the flaw of the prior art paddle shown in FIG. 13, wherein the vertical end wall of the paddle engaging the chest will occlude the X-ray beam when the paddle is tilted.

Figure 21A:
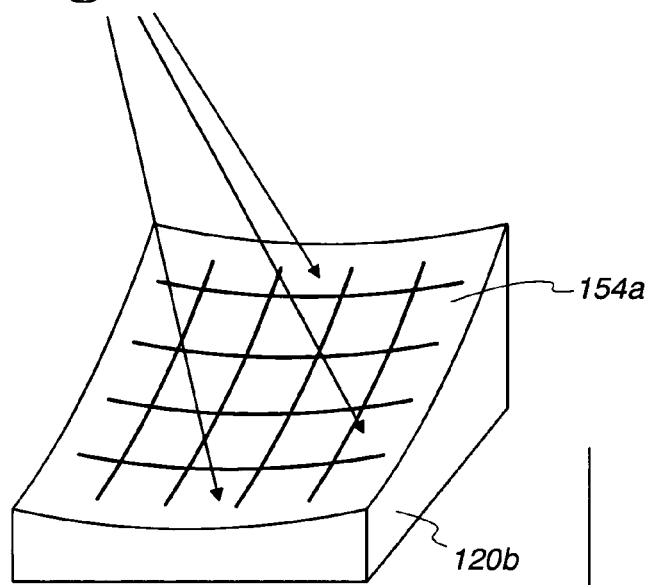
FIG. 21A shows an isomeric view of an embodiment of the invention wherein the bucky comprises a double convex or bowl-shaped surface.
Figure 21B:
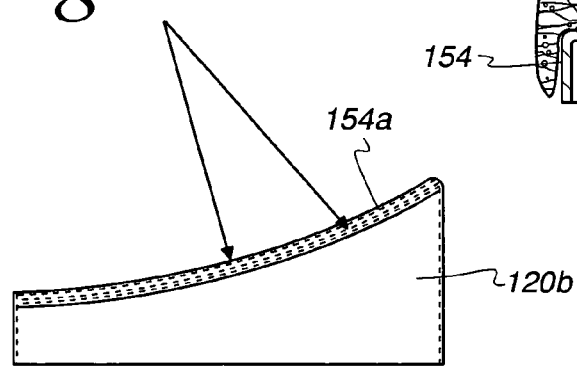
FIG. 21B shows a side view of the embodiment of FIG. 21A.

FIGS. 21A and 21B show a bucky 120B wherein the upper breast engaging surface 154 of the bucky is contoured essentially as a bowl to match a nominal 66 cm SID throughout the field of the X-ray beam or to substantially lessen the SID and the anterior breast. Contouring of the bucky 120B can compensate for the heel effect of the X-ray beam wherein the density and dosage of the beam is less on one edge of the field. Further, contouring of the bucky can be utilized to reduce parallax effects, particularly when using digital detectors rather than film.

Figure 22A:
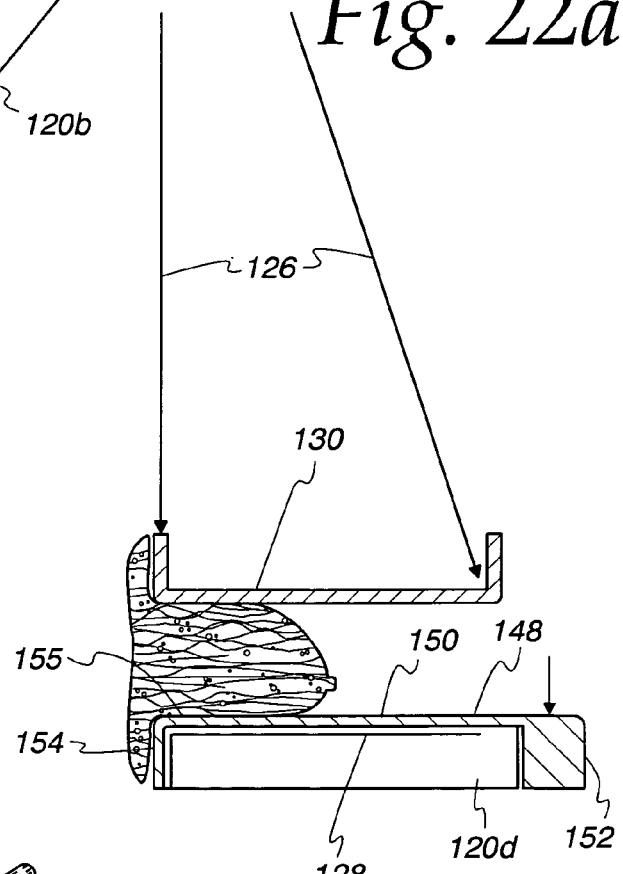
FIG. 22A shows an alternative embodiment of the invention wherein a tiltable cover is provided for the bucky, and the cover is shown in its horizontal position.

FIGS. 22A and 22B show an alternative embodiment of the invention comprising a tiltable bucky cover 148. FIG. 22A shows the bucky cover 148 mounted on bucky 120 with the cover 148 in its non-tilted position. Bucky cover 148 that may be formed of a carbon composite material which will not significantly attenuate the X-ray beams. The cover 148 includes a breast engaging upper surface plate 150, side walls 152 that extend downwardly over a portion of the side of the bucky and an end wall 154 that extends downwardly adjacent the patient's chest. The end wall 154 and a portion 150 about 2 cm in width along the edge of the plate 150 may be glue bonded to the bucky. The cover 148 thus has a portion 155 which is maintained in essentially a horizontal plane for approximately 2 cm to provide a vertically directed compression force as is desirable to prevent breast tissue from being pushed in toward the patient's chest wall. Preferably, the paddle is lowered to compress the breast tissue against the 2 centimeter portion 155 to compress the posterior breast tissue at the chest wall to prevent a subsequent pushing of posterior tissue from the imaging volume. The detectors in the lower horizontal stationary position of the bucky remain in a horizontal plane as is conventional. As shown in FIG. 22B, the bucky cover 148 is tiltable to compress the patient's breast in as similar advantageous manner as the structure of FIG. 14. A lead screw 140 and gear motor 142, as shown in FIGS. 15 and 16, provide the mechanism for tilting the bucky cover 150. The horizontal force component from the force applied by the tilted bucky cover portion will be insufficient to push the posterior breast tissue from the imaging volume. The bucky cover 148 may be most useful for retrofitting existing mammography machines to provide the features of the inventive system.

In an automated embodiment, the bucky and paddle may be driven vertically relative to one another to compress the breast therebetween and a compression force measuring system may be used to measure the breast compression at the chest wall to assure sufficient compression has been achieved to prevent posterior tissue from later being pushed from the imaging area and toward the chest wall. This measured limiting of posterior breast compression should also limit the amount of breast posterior skin displacement so that discomfiture is reduced. Then a controller may cause the motor drive to pivot the bucky to compress the middle and anterior breast portions. While the motor drive could be used in lieu of the internal spring, which is mounted in the paddle assembly, for pivoting the paddle section 29, it is preferred to use the internal spring for the paddle rather than the motor drive to pivot the section 29 and to compress the middle and anterior breast portion. The motor drive illustrated herein to drive the bucky could be used to drive the hinged section 29 relative to the fixed section 28 of the paddle.

While the invention has been particularly shown and described with reference to the preferred embodiments thereof, it will be understood by those skilled in the art that various changes in form and details may be made therein without departing from the spirit and scope of the invention.

What is claimed is:

1. In a method of X-ray mammography imaging of a breast at an imaging area, the breast having posterior tissue located at the chest wall and a middle and anterior tissue compressed between a paddle and bucky assembly on opposite sides of the breast, the method comprising:

displacing the paddle and bucky assembly relative to one another in the vertical direction to compress the posterior breast tissue at the chest wall in the vertical direction only without pushing posterior tissue at the chest wall away from the chest wall or into the chest wall and from the imaging area;

stopping this vertical displacement prior to compressing the anterior and middle breast portions sufficiently for imaging and in order to lessen the patient's discomfiture with further stretching of the posterior skin of the breast at a chest wall of the patient;

subsequently, in time, using an inclined surface on the paddle or bucky to compress the middle and anterior breast tissue with a second force which is at an angle to the first vertical force and which has a horizontal force component which is lesser than the first vertical force to prevent the anterior or middle breast tissue from pushing the posterior breast tissue toward the chest wall and from the imaging area;

imaging the compressed posterior, middle and anterior breast tissue;

using the paddle which has a fixed rigid section, which is X-ray transparent and which extends horizontally from the chest wall and which is positionable against the posterior breast tissue adjacent the chest wall to compress the posterior tissue to limit pushing of posterior breast tissue from the imaging area; and flexing an inclined section of the paddle joined at an outer end of the fixed rigid section to apply the subsequent second force through an inclined surface on the inclined section to compress the middle and anterior areas of the breast.

2. In a method of X-ray mammography imaging of a breast at an imaging area, the breast having posterior tissue located at the chest wall and a middle and anterior tissue compressed between a paddle and bucky assembly on opposite sides of the breast, the method comprising:

displacing the paddle and bucky assembly relative to one another in the vertical direction to compress the posterior breast tissue at the chest wall in the vertical direction only without pushing posterior tissue at the chest wall away from the chest wall or into the chest wall and from the imaging area;

stopping this vertical displacement prior to compressing the anterior and middle breast portions sufficiently for imaging and in order to lessen the patient's discomfiture with further stretching of the posterior skin of the breast at a chest wall of the patient;

subsequently, in time, using an inclined surface on the paddle or bucky to compress the middle and anterior breast tissue with a second force which is at an angle to the first vertical force and which has a horizontal force component which is lesser than the first vertical force to prevent the anterior or middle breast tissue from pushing the posterior breast tissue toward the chest wall and from the imaging area;

imaging the compressed posterior, middle and anterior breast tissue; and wherein the applying of the second, force to the middle and anterior breast areas comprises:

releasing a holding device which is holding a flexed, inclined paddle portion to allow the paddle portion to flex downwardly to automatically adjust a tilt angle to each patient's breast shape and density.

3. In a method of X-ray mammography imaging of a breast at an imaging area, the breast having posterior tissue located at the chest wall and a middle and anterior tissue compressed between a paddle and bucky assembly on opposite sides of the breast, the method comprising:

displacing the paddle and bucky assembly relative to one another in the vertical direction to compress the posterior breast tissue at the chest wall in the vertical direction only without pushing posterior tissue at the chest wall away from the chest wall or into the chest wall and from the imaging area;

stopping this vertical displacement prior to compressing the anterior and middle breast portions sufficiently for imaging and in order to lessen the patient's discomfiture with further stretching of the posterior skin of the breast at a chest wall of the patient;

subsequently, in time, using an inclined surface on the paddle or bucky to compress the middle and anterior breast tissue with a second force which is at an angle to the first vertical force and which has a horizontal force component which is lesser than the first vertical force to prevent the anterior or middle breast tissue from pushing the posterior breast tissue toward the chest wall and from the imaging area;

imaging the compressed posterior, middle and anterior breast tissue; and manually pulling downwardly the flexed inclined paddle portion to apply additional compression for middle and anterior breast tissue when desired by an operator; and operating the holding device to retain the flexed portion in the position to apply this additional compression to the middle and anterior breast tissue.

4. In a method of X-ray mammography imaging of a breast at an imaging area, the breast having posterior tissue located at the chest wall and a middle and anterior tissue compressed between a paddle and bucky assembly on opposite sides of the breast, the method comprising:

displacing the paddle and bucky assembly relative to one another in the vertical direction to compress the posterior breast tissue at the chest wall in the vertical direction only without pushing posterior tissue at the chest wall away from the chest wall or into the chest wall and from the imaging area;

stopping this vertical displacement prior to compressing the anterior and middle breast portions sufficiently for imaging and in order to lessen the patient's discomfiture with further stretching of the posterior skin of the breast at a chest wall of the patient;

subsequently, in time, using an inclined surface on the paddle or bucky to compress the middle and anterior breast tissue with a second force which is at an angle to the first vertical force and which has a horizontal force component which is lesser than the first vertical force to prevent the anterior or middle breast tissue from pushing the posterior breast tissue toward the chest wall and from the imaging area;

imaging the compressed posterior, middle and anterior breast tissue;

applying the first vertical force to the posterior breast by opposite surfaces which are extending for a few centimeters from the chest wall of the patient to apply the vertical forces over substantial surfaces on each side of the posterior breast tissue at the chest wall; and pivoting an inclined section on a support, which is located outwardly of the horizontal section to apply the subsequent and angled second force to compress the middle and anterior areas against the paddle.

5. In a method of X-ray mammography imaging of a breast at an imaging area, the breast having posterior tissue located at the chest wall and a middle and anterior tissue compressed between a paddle and bucky assembly on opposite sides of the breast, the method comprising:

displacing the paddle and bucky assembly relative to one another in the vertical direction to compress the posterior breast tissue at the chest wall in the vertical direction only without pushing posterior tissue at the chest wall away from the chest wall or into the chest wall and from the imaging area;

stopping this vertical displacement prior to compressing the anterior and middle breast portions sufficiently for imaging and in order to lessen the patient's discomfiture with further stretching of the posterior skin of the breast at a chest wall of the patient;

subsequently, in time, using an inclined surface on the paddle or bucky to compress the middle and anterior breast tissue with a second force which is at an angle to the first vertical force and which has a horizontal force component which is lesser than the first vertical force to prevent the anterior or middle breast tissue from pushing the posterior breast tissue toward the chest wall and from the imaging area;

imaging the compressed posterior, middle and anterior breast tissue;

a bucky assembly pivotally mounted and movable to an inclined position to apply the second force to compress the middle and anterior breast tissue;

imaging the breast with detectors on the bucky assembly; and pivoting the bucky assembly to position detectors thereon closer to the X-ray source to reduce the heel effect of the longer incident X-rays from the heel of the x-ray tube.

6. A method of compressing a breast having posterior, middle and anterior tissue between a paddle and a bucky assembly for mammographic imaging of the breast at an imaging area, the method comprising:

providing a paddle with a compression surface at the upper side of the breast and a bucky having a compression surface at the bottom side of the breast;

one of said bucky and paddle surfaces having an inclined compression surface;

moving the opposed surfaces relative to one another to compress the posterior portion of the breast adjacent the chest wall between the compression surfaces with a first vertically directed force to force the posterior breast surface to prevent a substantial shifting of the breast tissue in a horizontal direction toward or from the chest wall;

compressing the middle and anterior portions of the breast with a second force from the inclined compression surface to compress the anterior and middle breast tissue;

the compressed posterior tissue receiving a horizontally directed force component urging the compressed posterior tissue to move horizontally toward the chest wall and from the imaging area;

the first force holding the vertically compressed tissue against the horizontal displacement from the imaging area adjacent the chest wall by the horizontally directed component provided by the inclined compression surface; and wherein the applying of the second, compression force to the middle and anterior breast tissue comprises:

releasing a device holding a flexed inclined portion to flex downwardly to automatically adjust the tilt angle to each patient's breast shape and density.

7. A method in accordance with claim 6 comprising:

manually pulling downwardly the flexed inclined portion to apply additional compression for middle and anterior breast portions when desired by an operator; and operating a holding device to retain the flexed portion in the position to apply this additional compression to the middle anterior breast areas.

8. A method of compressing a breast having posterior, middle and anterior tissue between a paddle and a bucky assembly for mammographic imaging of the breast, the method comprising:

providing a paddle with a compression surface at the upper side of the breast and a bucky having a compression surface at the bottom side of the breast;

one of said bucky and paddle surfaces having an inclined compression surface;

moving the opposed surfaces relative to one another to compress the posterior portion of the breast adjacent the chest wall between the compression surfaces with a first vertically directed force to force the posterior breast surface to prevent a substantial shifting of the breast tissue in a horizontal direction toward or from the chest wall;

compressing the middle and anterior portions of the breast with a second force from the inclined compression surface to compress the anterior and middle breast tissue;

the compressed posterior tissue receiving a horizontally directed force component urging it to move horizontally toward the chest wall and from the imaging area;

the first force holding the vertically compressed tissue against the horizontal displacement from the imaging area adjacent the chest wall by the horizontally directed component provided by the inclined compression surface; and compressing the breast tissue with the inclined compression surface located on the bucky assembly and hinged at a location away from the X-ray source so that the hinge does not obstruct the imaging of the posterior breast tissue where the breast joins the chest wall.

9. A method in accordance with claim 8 comprising:

providing an X-ray imaging detector on the bucky assembly;

positioning an imaging detector located at a anterior portion of the bucky assembly to be closer to the X-ray source than it would be when in a horizontal plane located at the portion of the detector at the chest wall so that the distance between a heel portion of the X-ray source and the anterior area detector portion is shortened for those lesser energy incident rays emanating from a heel of an X-ray source and traveling through the breast to the inclined detector portion.

10. A method in accordance with claim 9 comprising:

positioning the anterior area, inclined detector portion in the range of at least about three centimeters or more closer to the X-ray source than if it were in a horizontal plane.

11. A method of compressing a breast having posterior, middle and anterior tissue between a paddle and a bucky assembly for mammographic imaging of the breast, the method comprising:

providing a paddle with a compression surface at the upper side of the breast and a bucky having a compression surface at the bottom side of the breast;

one of said bucky and paddle surfaces having an inclined compression surface;

moving the opposed surfaces relative to one another to compress the posterior portion of the breast adjacent the chest wall between the compression surfaces with a first vertically directed force to force the posterior breast surface to prevent a substantial shifting of the breast tissue in a horizontal direction toward or from the chest wall;

compressing the middle and anterior portions of the breast with a second force from the inclined compression surface to compress the anterior and middle breast tissue;

the compressed posterior tissue receiving a horizontally directed force component urging it to move horizontally toward the chest wall and from the imaging area;

the first force holding the vertically compressed tissue against the horizontal displacement from the imaging area adjacent the chest wall by the horizontally directed component provided by the inclined compression surface;

applying the vertical compression force to opposite sides of the breast first with a compression force extending for a few centimeters from the chest wall to compress the breast tissue with the first vertical compression force over areas extending horizontally a few centimeters outwardly of the chest wall; and subsequently applying the second force beginning at an outward end of the first compression force to the middle and anterior areas to compress them with the component of the second force being normal to the chest wall and being insufficient to force the initially compressed posterior tissue towards the ribs and out of the imaging area.

12. A method in accordance with claim 11 comprising:

first using a paddle with a horizontal portion extending outwardly of the chest wall for at least a few centimeters to apply a first vertical compression force over an area located outwardly for a few centimeters from the chest wall; and subsequently flexing an inclined, hinged portion on the paddle, which is X-ray transparent, to provide the second compression force at the middle and anterior areas of the breast.

13. A method in accordance with claim 12 wherein the applying of the second, compression force to the middle and anterior breast tissues comprises:

releasing a device holding a flexed inclined portion to flex downwardly to automatically adjust the tilt angle to the patient's breast shape and density.

14. A method in accordance with claim 12 comprising:

manually pulling downwardly the flexed inclined portion to apply additional compression for middle and anterior breast portions when desired by an operator; and operating the holding device to retain the flexed portion in the position to apply this additional compression to the middle anterior breast tissues.

15. A method of compressing a breast having posterior, middle and anterior tissue between a paddle and a bucky assembly for mammographic imaging of the breast, the method comprising:

providing a paddle with a compression surface at the upper side of the breast and a bucky having a compression surface at the bottom side of the breast;

one of said bucky and paddle surfaces having an inclined compression surface;

moving the opposed surfaces relative to one another to compress the posterior portion of the breast adjacent the chest wall between the compression surfaces with a first vertically directed force to force the posterior breast surface to prevent a substantial shifting of the breast tissue in a horizontal direction toward or from the chest wall;

compressing the middle and anterior portions of the breast with a second force from the inclined compression surface to compress the anterior and middle breast tissue;

the compressed posterior tissue receiving a horizontally directed force component urging it to move horizontally toward the chest wall and from the imaging area;

the first force holding the vertically compressed tissue against the horizontal displacement from the imaging area adjacent the chest wall by the horizontally directed component provided by the inclined compression surface; and the first compression force being in the range of 25 to 40 pounds and the subsequent, second compression force is in the range of about 10 to 15 pounds.

16. A method in accordance with claim 13 comprising:

providing a hinged, inclined bucky assembly having a horizontal compression surface thereon to apply the first, vertical compression force to the posterior breast portion adjacent the chest wall, the bucky assembly having an inclined hinged portion with the inclined compression surface to provide the subsequent and second compression force at the middle and anterior areas of the breast.

17. A method in accordance with claim 15 comprising:

providing an upper cover portion on the bucky assembly with the flat section surface and an inclined section surface; and providing detectors for imaging on the bucky assembly below the cover portion.

18. A method of improving compression of the middle and interior breast tissue in a mammography system and for lessening of a heel effect of X-rays from a heel of an X-ray source, the method comprising:

moving a bucky assembly having an image detector and a paddle relative to one another to compress, with a first force, the posterior breast tissue adjacent the chest wall;

tilting an anterior end portion of the bucky assembly toward the paddle to provide a second compressive force to compress the middle and anterior breast tissue;

exposing the breast to X-ray beams to image in the breast; and moving the bucky assembly and paddle relative to each other to release compression of the breast.

19. A method in accordance with claim 18 comprising:

positioning a portion of an X-ray detector on the anterior end portion of the bucky assembly closer to the X-ray source to lessen the heel effect of incident X-rays at the anterior breast tissue.

20. A method in accordance with claim 19 comprising:

holding the compressed posterior breast tissue adjacent the chest wall with a first compression force larger than a horizontal vector force from the second compression force at the middle and anterior breast tissue to prevent displacement of the posterior breast tissue from the imaging area.

21. A method of compression of middle and anterior breast tissue in a mammography system having a paddle for pressing on the breast on the X-ray source side of the breast and having a bucky assembly on the other side of the breast, the method comprising:

providing a tiltable cover on the bucky assembly with the tiltable cover being transparent to the X-ray beams;

moving a first portion on the tiltable cover relative to the paddle to provide a compression of the posterior breast tissue adjacent the chest wall;

tilting the tiltable cover toward the paddle to provide additional compression of the middle and anterior breast tissue; and exposing the breast to X-ray beams to image lesions in the breast.

22. A method in accordance with claim 21 comprising:

holding the compressed posterior breast tissue adjacent the chest wall with a first compression force which is greater than a horizontal vector of the additional compression force at the middle and anterior breast tissue to prevent displacement of the posterior breast tissue from the imaging area.

23. In a method of providing a mammogram with an image at the posterior breast tissue at the chest wall and at breast middle and anterior tissues, the method comprises:

providing a paddle for overlying the breast;

providing a bucky assembly pivotably mounted for breast compression;

moving the bucky assembly relative to the paddle and applying a compression force to compress the breast; and directing an X-ray beam through the compressed breast tissue to image the breast.

24. In an apparatus for X-ray mammography imaging of a breast having posterior tissue located at the chest wall and a middle and anterior tissue without obstructing the imaging of the breast comprising:

an X-ray source for applying X-rays to image the breast;

a paddle located between the X-ray source and the breast;

a compressing surface on the paddle being transparent to X-rays without an occluding hinge or portion of the paddle in the mammography image of the breast;

a bucky assembly on a side of the breast opposite the paddle and having a compression surface engaging the breast;

a drive for shifting the paddle compressive surface and bucky compression surface relative to one another to compress the breast therebetween;

said compressive surfaces compressing the posterior breast tissue adjacent the chest wall with vertically directed force only without pushing the posterior breast tissue away from the chest wall and to compress this posterior breast tissue sufficiently to lessen any subsequent pushing of breast tissue toward the chest wall; and an inclined compressive surface portion on one of the compressive surfaces for subsequently, in time, applying a second compression force to compress the middle and anterior breast tissue with a second force which is at an angle to the first force and which has a horizontal component lesser than the first vertical force to limit pushing of posterior breast tissue toward the chest wall;

the paddle having a first fixed, substantially horizontal portion projecting outwardly from the chest wall to apply the first compressive force at the posterior breast; and a flexible portion on the paddle joined to an end of the first portion of the paddle at a pivot location substantially outwardly of the chest wall pivotable from a first position to a second inclined position with respect to the horizontal fixed portion to apply the second compressive force to the middle and anterior portions of the breast.

25. An apparatus in accordance with claim 24 comprising:

an X-ray transparent hinge portion on the paddle joining the chest wall projecting portion and the inclined portion for hinging movement of the inclined portion relative to the projecting portion.

26. In an apparatus for X-ray mammography imaging of a breast having posterior tissue located at the chest wall and a middle and anterior tissue without obstructing the imaging of the breast comprising:

an X-ray source for applying X-rays to image the breast;

a paddle located between the X-ray source and the breast;

a compressing surface on the paddle being transparent to X-rays without an occluding hinge or portion of the paddle in the mammography image of the breast;

a bucky assembly on a side of the breast opposite the paddle and having a compression surface engaging the breast;

a drive for shifting the paddle compressive surface and bucky compression surface relative to one another to compress the breast therebetween;

said compressive surfaces compressing the posterior breast tissue adjacent the chest wall with vertically directed force only without pushing the posterior breast tissue away from the chest wall and to compress this posterior breast tissue sufficiently to lessen any subsequent pushing of breast tissue toward the chest wall;

an inclined compressive surface portion on one of the compressive surfaces for subsequently, in time, applying a second compression force to compress the middle and anterior breast tissue with a second force which is at an angle to the first force and which has a horizontal component lesser than the first vertical force to limit pushing of posterior breast tissue toward the chest wall;

the paddle having a first substantially horizontal portion projecting outwardly from the chest wall to apply the first compressive force at the posterior breast;

an inclined portion on the paddle joined to an end of the first portion of the paddle at a location substantially outwardly of the chest wall to apply the second compressive force to the middle and anterior portions of the breast;

an X-ray transparent hinge portion on the paddle joining the chest wall projecting portion and the inclined portion for hinging movement of the inclined portion relative to the projecting portion;

the inclined portion being biased to flex to engage and compress the breast; and a releasable holding device holding the inclined portion in its flexed position until the holding device is shifted to a release position releasing the inclined portion to flex to compress the breast.

27. In an apparatus for X-ray mammography imaging of a breast having posterior tissue located at the chest wall and a middle and anterior tissue without obstructing the imaging of the breast comprising:

an X-ray source for applying X-rays to image the breast;

a paddle located between the X-ray source and the breast;

a compressing surface on the paddle being transparent to X-rays without an occluding hinge or portion of the paddle in the mammography image of the breast;

a bucky assembly on a side of the breast opposite the paddle and having a compression surface engaging the breast;

a drive for shifting the paddle compressive surface and bucky compression surface relative to one another to compress the breast therebetween;

said compressive surfaces compressing the posterior breast tissue adjacent the chest wall with vertically directed force only without pushing the posterior breast tissue away from the chest wall and to compress this posterior breast tissue sufficiently to lessen any subsequent pushing of breast tissue toward the chest wall; and an inclined compressive surface portion on one of the compressive surfaces for subsequently, in time, applying a second compression force to compress the middle and anterior breast tissue with a second force which is at an angle to the first force and which has a horizontal component lesser than the first vertical force to limit pushing of posterior breast tissue toward the chest wall;

the bucky assembly having the inclined portion for compressing the anterior and middle breast portions; and a pivot mounting on the bucky assembly for pivotal movement of the bucky assembly to compress the anterior and middle portion of the breast.

28. In an apparatus for X-ray mammography imaging of a breast having posterior tissue located at the chest wall and a middle and anterior tissue without obstructing the imaging of the breast comprising:

an X-ray source for applying X-rays to image the breast;

a paddle located between the X-ray source and the breast;

a compressing surface on the paddle being transparent to X-rays without an occluding hinge or portion of the paddle in the mammography image of the breast;

a bucky assembly on a side of the breast opposite the paddle and having a compression surface engaging the breast;

a drive for shifting the paddle compressive surface and bucky compression surface relative to one another to compress the breast therebetween;

said compressive surfaces compressing the posterior breast tissue adjacent the chest wall with vertically directed force only without pushing the posterior breast tissue away from the chest wall and to compress this posterior breast tissue sufficiently to lessen any subsequent pushing of breast tissue toward the chest wall;

an inclined compressive surface portion on one of the compressive surfaces for subsequently, in time, applying a second compression force to compress the middle and anterior breast tissue with a second force which is at an angle to the first force and which has a horizontal component lesser than the first vertical force to limit pushing of posterior breast tissue toward the chest wall;

the bucky assembly having the inclined portion for compressing the anterior and middle breast portions;

a pivot mounting on the bucky assembly for pivotal movement of the bucky assembly to compress the anterior and middle portion of the breast;

the drive comprising a first vertical drive to shift the paddle and bucky in a vertical direction to compress the posterior breast portion; and the drive comprises a second drive for shifting the inclined portion on the bucky assembly to compress the anterior and middle breast portions.

29. In an apparatus for X-ray mammography imaging of a breast having posterior tissue located at the chest wall and a middle and anterior tissue without obstructing the imaging of the breast comprising:

an X-ray source for applying X-rays to image the breast;

a paddle located between the X-ray source and the breast;

a compressing surface on the paddle being transparent to X-rays without an occluding hinge or portion of the paddle in the mammography image of the breast;

a bucky assembly on a side of the breast opposite the paddle and having a compression surface engaging the breast;

a drive for shifting the paddle compressive surface and bucky compression surface relative to one another to compress the breast therebetween;

said compressive surfaces compressing the posterior breast tissue adjacent the chest wall with vertically directed force only without pushing the posterior breast tissue away from the chest wall and to compress this posterior breast tissue sufficiently to lessen any subsequent pushing of breast tissue toward the chest wall;

the bucky assembly having the inclined portion for compressing the anterior and middle breast portions; and the bucky assembly comprising a detector for the X-rays and the detector is shifted toward the X-ray source to shorten the distance between the detector at the anterior breast and the X-ray source.

30. A bucky for use with an X-ray mammography machine wherein said machine includes a bucky and a compression paddle for compressing a patient's breast therebetween, said bucky being controllably tiltable in relation to said compression paddle.

31. A bucky as in claim 30 wherein said bucky is pivotable on a pivot point that enables the bucky to compress an extended area of the breast extending toward the nipple end of the breast.

32. A bucky as in claim 30 that includes a pivoting mechanism that has a pivot point external of the pivoting mechanism.

33. A bucky as in claim 30 including a drive mechanism for controllably moving said bucky from a first position to a selected second position angled with respect to said first position.

34. A bucky for use with an X-ray mammography machine wherein said machine includes a bucky and a compression paddle for compressing a patient's breast therebetween, said bucky including a cover that is controllably tiltable in relation to said compression paddle.

35. An X-ray mammography machine including:
a frame;
a bucky;
a pivot connection between the frame and the bucky;
a compression paddle;
wherein the bucky and compression paddle are movable relative to one another, and
wherein said bucky is pivoted toward the paddle to provide an extended area of breast compression between the paddle and the pivoted bucky.

36. A breast compression paddle for use with an X-ray machine, said paddle being positionable over a patient's breast for compressing said breast for the taking of mammography images comprising:

a tray-like member formed of rigid, radiolucent plastic having a bottom surface and a wall form around the periphery of said bottom surface;

said bottom surface comprising a fixed, rigid section positionable over the immediate area of the patient's chest wall and a second rigid but flexible section extending from said fixed section;

said first and second sections having a common band of plastic material, and said second section being flexible and bendable on said common band;

a biasing spring mechanism for providing a selected force to said flexible section; and whereby in operation said paddle compresses the patient's breast with an essentially vertically downward force in the immediate area of the breast wall and compresses the patient's breast toward the nipple of the breast with a downwardly angled surface.

37. A breast compression paddle as in claim 36 wherein said bottom surface is flexible along said band, and the opposite side of said flexible section is affixed to said adjustable spring mechanism to enable said flexible section to angle downwardly.

38. A breast compression paddle as in claim 37 wherein: said spring mechanism enables said flexible surface to flex downwardly at an adjustable angle of a maximum of about 15□ from the horizontal.

39. A breast compression paddle as in claim 36 further including an aperture in said walls to form a flexing area, said aperture enabling the walls to have minimal stress when said second section is flexed, and manual means for adjusting said spring mechanism.

40. A breast compression paddle for use with a mammography machines that provides an X-ray beam, said paddle having a spring force, said paddle being positionable adjacent a female person's breast, said paddle having a lower surface for pressing against said breast, a first section of said lower surface adjacent said chest wall being fixed, a second section of said lower surface being flexible along a band of said first section, and said lower surface being flexible only from a position substantially spaced from said chest wall to maintain said breast steady during the taking of an X-ray image.

41. A breast compression paddle as in claim 40 wherein said paddle is made as a rectangular tray-like structure of five sides wherein one side comprises a rigid member that is flexible along a band.

42. A breast compression paddle as in claim 41 wherein said lower surface of the paddle engages the breast at an angle of up to about 15°, and the end of the paddle adjacent the chest wall will not be movable within the area of the X-ray beam.

43. A breast compression paddle as in claim 42 further including a manually responsive spring mechanism for applying force to said breast.

44. A paddle for use in a mammographic machine and for compressing anterior, middle and posterior breast tissue comprising:
- a first posterior fixed section having a surface extending outwardly of the chest wall for compressing the posterior breast tissue outwardly of the chest wall;
- an anterior section on the paddle extending from the fixed posterior section for positioning against the anterior breast tissue to compress the same; and
- an X-ray transparent hinge section on the paddle between the posterior section and the anterior section at a location outwardly of the chest wall for hinging the sections together for relative movement to each other, the hinge section extending over the breast and allowing X-rays to pass the hinge section without causing a shadow on the X-ray image of the breast.

45. A paddle for use in a mammographic machine and for compressing anterior, middle and posterior breast tissue comprising:
- a first posterior section having a surface for compressing the posterior breast tissue;
- a flexed section biased to move to an inclined position against the middle and anterior breast tissue to compress the same;
- an X-ray transparent hinge section on the paddle between the posterior section and the flexed section for hinging the sections together, the hinge section extending over the breast and allowing X-rays to pass therethrough without causing a shadow on the X-ray image of the breast; and
the X-ray transparent hinge section comprising a band of bendable plastic that bends and conforms to the breast shape.

46. A paddle in accordance with claim 45 wherein the paddle has plastic posterior and flexed sections:
the hinge section being a living hinge formed of the same plastic as the posterior and flexed sections.

47. A paddle for use in a mammographic machine and for compressing anterior, middle and posterior breast tissue comprising:
- a first posterior section on the x-ray paddle extending outwardly from the chest wall for a predetermined distance and having a surface for compressing the posterior breast tissue adjacent the chest wall;
- an anterior section on the x-ray paddle for compressing the anterior portion of the breast extending outwardly from an outer end of the posterior section;
- a flexible hinge section of plastic joining together the posterior and anterior sections of the paddle for relative movement with respect to each other;
- the hinge section covering a portion of the breast and being transparent to x-rays at the covered portion allowing x-ray imaging of the breast under the hinge section; and
- the hinge section allowing the anterior and posterior sections to change the angle of inclination between the posterior and anterior sections of the paddle for compression of the respective middle and anterior portions of the breast with the inclined anterior section of the paddle.

48. A paddle in accordance with claim 47 wherein the hinge section comprises:
a living hinge and integrally formed of the same plastic as the plastic anterior and posterior sections.

49. A paddle in accordance with claim 47 comprising:
the posterior section extending outwardly from the chest wall for a distance of a few centimeters and then joins the hinge section, the posterior section compressing a few centimeters of posterior breast tissue to hold this posterior tissue to lessen displacement into the chest wall by an inclined anterior section compressing the anterior portion of the breast.

50. A paddle in accordance with claim 47 wherein the anterior, posterior and hinge sections has a cross-section thickness of about 0.075 to about 0.095 inch.

51. A paddle in accordance with claim 47 comprising:
guiding the second section in its movement to provide a level compression surface across the width of the breast for breasts positioned off-center with respect to the paddle.

52. A method of compressing a breast having posterior, middle and anterior tissue between an x-ray treatment paddle on one side of a breast and a support on the opposite side of the breast for mammographic imaging of the breast, the method comprising:
providing a paddle with a first section adjacent the chest wall for compressing the tissue of the posterior breast tissue with a first compression force over a posterior area extending outwardly of the chest wall for a predetermined distance and providing a moveable second section on the paddle joined to the first rigid section at a common point spaced outwardly of the chest wall by a predetermined distance of at least several centimeters, the second section being movable relative to the first section for compression of the middle and anterior tissue with a lesser compression force which is less than the first compression force;

compressing the posterior portion of the breast adjacent to and outwardly of the chest wall for the predetermined distance with the first section of the paddle with the first compression force to hold the posterior breast tissue to lessen its displacement into the chest wall; and moving the second section relative to the fixed section at the common point therebetween and compressing the middle and anterior portions of the breast tissue that is located outwardly of the common point with the second section of the paddle with the second lesser force.

53. A method in accordance with claim 52 comprising:

providing a flexible, integral hinge portion on the paddle between the first rigid section and moveable second section for hinging the second section for movement relative to the first section; and compressing the breast tissue underlying the hinge portion with the hinge.

54. A method in accordance with claim 52 comprising:

compressing the anterior breast tissue with a first force in the range of about 25 to 40 lbs and with a second force in the range of 1–15 lbs.

55. A method in accordance with claim 52 comprising:

compressing the posterior tissue over several centimeters outwardly of the chest wall with a sufficient first force to prevent the second compression force from pushing the posterior tissue at the chest wall from the x-ray imaging area.

* * * * *